United States Patent [19]

Stacker et al.

[11] Patent Number: 6,107,472

[45] Date of Patent: Aug. 22, 2000

[54] RECEPTOR-TYPE TYROSINE KINASE-LIKE MOLECULES

[75] Inventors: Steven A. Stacker, North Fitzroy, Australia; Christopher M. Hovens, Zurich, Switzerland; Andrew F. Wilks, Doncaster East, Australia

[73] Assignee: Ludwig Institute for Cancer Research, New York, N.Y.

[21] Appl. No.: 08/335,865

[22] PCT Filed: May 10, 1993

[86] PCT No.: PCT/AU93/00210

§ 371 Date: Jan. 19, 1995

§ 102(e) Date: Jan. 19, 1995

[87] PCT Pub. No.: WO93/23429

PCT Pub. Date: Nov. 25, 1993

[30] Foreign Application Priority Data

May 11, 1992 [AU] Australia ................................ PL2358

[51] Int. Cl.[7] ...................... C07K 14/435; C07K 14/705; C12N 15/12; C12N 15/54
[52] U.S. Cl. ............................ 536/23.5; 530/350
[58] Field of Search ........................ 530/350; 435/69.1, 435/6, 184, 320.1; 536/23.5, 23.2

[56] References Cited

PUBLICATIONS

Maminta, M.L.D. et al., *BBRC*, 189(2): 1077–83, Dec., 1992.
Partanen, J. et al., *PNAS*, 87: 8913–8919, 1990.
Hanks et al., *Science*, 241 : 42–52, 1988.
Yeung et al., *PNAS*, 84 : 1268–1271, 1987.
Kozak, *NAR*, 12 : 857–872, 1984.
Bishop, Ann. Rev. Biochem., 52 : 301–354, 1983.
Wilks, *Advances Canc. Res.*, 60 : 43–73, 1992.
Chou et al., *PNAS*, 88 : 4897–4901, 1991.
Knighton et al., *Science*, 253 : 407–414, 1991.
Ulrich et al., *Cell*, 61 : 203–212, 1990.
Carpenter et al., *JBC*, 265 : 7709–7712, 1990.
Resh, *Oncogenes*, 1437–1444, 1990.
Williams, *Science*, 243 : 1564–1570, 1989.
Yarden, et al., *Ann. Rev. Biochem.*, 57 : 443–478, 1988.

*Primary Examiner*—Marianne P. Allen
*Attorney, Agent, or Firm*—Fulbright & Jaworski, LLP

[57] ABSTRACT

The present invention relates to proteins having receptor-type tyrosine kinase-like properties which represent a novel family of proteins related to protein tyrosine kinases. The present invention relates to the full length proteins and to subunits, mutants, derivatives and/or analogues thereof and to nucleotide sequences encoding same. The present invention also extends to ligands for the above proteins and to pharmaceutical compositions comprising the proteins and/or mutants, derivatives and/or analogues thereof and/or ligands thereto.

12 Claims, 25 Drawing Sheets

FIG. 2B-1

```
    AAC GGT ATC GAT AAG CTT GAT ATC GAA TTC CGC ACC CCC GGC
            10          20          30          40
TCG GGG CTG TGA GCG GCT CGG GGC CGG GGG TGG GCG GCG GTG CGG
            54          64          74          84
CGG GCG GCC GAC GCT CCT CTT CGG CGG CGG CGG CGG CGG CGG CCC
            99         109         119         129

Met Arg Gly Ala Ala Arg Leu Gly Arg Pro Gly Arg Ser Cys Leu
ATG CGT GGG GCG GCG CGG CTG GGG CGG CCG GGC CGG AGT TGC CTC
            144         154         164         174

Pro Gly Pro Ala Leu Arg Ala Ala Ala Pro Ala Leu Leu Leu
CCG GGG CCC GCC CTG AGG GCC GCC GCC GCG CCC GCC CTG CTG CTT
            189         199         209         219

Ala Arg Cys Ala Val Ala Ala Ala Gly Leu Arg Ala Ala Ala
GCT CGT TGC GCT GTT GCC GCT GCT GCC GGC CTG CGT GCC GCC GCC
            234         244         254         264

Arg Pro Arg Pro Pro Glu Leu Gln Ser Ala Ser Ala Gly Pro Ser
CGT CCC CGG CCC CCG GAG CTG CAG TCG GCT TCC GCG GGG CCC AGC
            279         289         299         309

Val Ser Leu Tyr Leu Ser Glu Asp Glu Val Arg Arg Leu Ile Gly
GTG AGT CTC TAC CTG AGC GAG GAC GAG GTG CGC CGG CTG ATC GGT
            324         334         344         354

Leu Asp Ala Glu Leu Tyr Tyr Val Arg Asn Asp Leu Ile Ser His
CTT GAT GCA GAA CTT TAT TAT GTG AGA AAT GAC CTT ATT AGT CAC
            369         379         389         399

Tyr Ala Leu Ser Phe Asn Leu Leu Val Pro Ser Glu Thr Asn Phe
TAC GCT CTA TCC TTT AAT CTG TTA GTA CCC AGT GAG ACA AAT TTC
            414         424         434         444

Leu His Phe Thr Trp His Ala Lys Ser Lys Val Glu Tyr Lys Leu
CTG CAC TTC ACC TGG CAT GCG AAG TCC AAG GTT GAA TAT AAG CTG
            459         469         479         489

Gly Phe Gln Val Asp Asn Val Leu Ala Met Asp Met Pro Gln Val
GGA TTC CAA GTG GAC AAT GTT TTG GCA ATG GAT ATG CCC CAG GTC
            504         514         524         534

Asn Ile Ser Val Gln Gly Glu Val Pro Arg Thr Leu Ser Val Phe
AAC ATT TCT GTT CAG GGG GAA GTT CCA CGC ACT TTA TCA GTG TTT
            549         559         569         579

Arg Val Glu Leu Ser Cys Thr Gly Lys Val Asp Ser Glu Val Met
CGG GTA GAG CTT TCC TGT ACT GGC AAA GTA GAT TCT GAA GTT ATG
            594         604         614         624
```

FIG. 2B-2

```
Ile Leu Met Gln Leu ⌐Asn  Leu Thr⌐ Val ⌐Asn Ser Ser⌐ Lys ⌐Asn Phe
ATA CTA ATG CAG CTC  AAC  TTG ACA  GTA  AAT TCT TCA  AAA  AAT TTT
             639          649          659          669

⌐Thr⌐ Val Leu Asn Phe Lys Arg Arg Lys Met (Cys) Tyr Lys Lys Leu
 ACC  GTC TTA AAT TTT AAA CGA AGG AAA ATG  TGC  TAC AAA AAA CTT
              684         694             704          714

Glu Glu Val Lys Thr Ser Ala Leu Asp Lys Asn Thr Ser Arg Thr
GAA GAA GTA AAA ACT TCA GCC TTG GAC AAA AAC ACT AGC AGA ACT
            729         739         749         759

Ile Tyr Asp Pro Val His Ala Ala Pro Thr Thr Ser Thr Arg Val
ATT TAT GAT CCT GTA CAT GCA GCT CCA ACC ACT TCT ACG CGT GTG
            774         784         794         804

Phe Tyr Ile Ser Val Gly Val (Cys) (Cys) Ala Val Ile Phe Leu Val
TTT TAT ATT AGT GTA GGG GTT  TGT   TGT  GCA GTA ATA TTT CTC GTA
            819         829             839         849

Ala Ile Ile Leu Ala Val Leu His Leu His Asn Met Lys Arg Ile
GCA ATA ATA TTA GCT GTT TTG CAC CTT CAT AAT ATG AAA AGG ATT
            864         874         884         894

Glu Leu Asp Asp Ser Ile Ser Ala Ser Ser Ser Gln Gly Leu
GAA CTG GAT GAC AGC ATT AGT GCC AGC AGT AGT TCC CAA GGG CTG
            909         919         929         939

Ser Gln Pro Ser Thr Gln Thr Thr Glu Tyr Leu Arg Ala Asp Thr
TCT CAG CCA TCC ACC CAG ACG ACT CAG TAT CTG AGA GCA GAC ACG
            954         964         974         984

Pro Asn Asn Ala Thr Pro Ile Thr Ser Tyr Pro Thr Leu Arg Ile
CCC AAC AAT GCA ACT CCT ATC ACC AGT TAT CCT ACC TTG CGG ATA
            999         1009        1019        1029

Glu Lys Asn Asp Leu Arg Ser Val Thr Leu Leu Glu Ala Lys Gly
GAG AAG AAC GAC TTG AGA AGT GTC ACT CTT TTG GAG GCC AAA GGC
            1044        1054        1064        1074

Lys Val Lys Asp Ile Ala Ile Ser Arg Glu Arg Ile Thr Leu Lys
AAG GTG AAG GAT ATA GCA ATA TCC AGA GAG AGG ATA ACT CTA AAA
            1089        1099        1109        1119

Asp Val Leu Gln Glu Gly Thr Phe Gly Arg Ile Phe His Gly Ile
GAT GTA CTC CAA GAA GGT ACT TTT GGG CGT ATT TTC CAT GGG ATT
            1134        1144        1154        1164

Leu Ile Asp Glu Lys Asp Pro Asn Lys Glu Lys Gln Ala Phe Val
TTA ATA GAT GAA AAA GAT CCA AAT AAA GAA AAA CAA GCA TTT GTC
            1179        1189        1199        1209
```

FIG. 2B-3

```
Lys Thr Val Lys Asp Gln Ala Ser Glu Ile Gln Val Thr Met Met
AAA ACA GTT AAA GAT CAA GCT TCT GAA ATT CAG GTG ACA ATG ATG
        1224        1234        1244        1254

Leu Thr Glu Ser Cys Lys Leu Arg Gly Leu His His Arg Asn Leu
CTC ACT GAA AGT TGT AAG CTG CGA GGT CTT CAT CAC AGA AAT CTT
        1269        1279        1289        1299

Leu Pro Ile Thr His Val Cys Ile Glu Glu Gly Glu Lys Pro Met
CTT CCT ATT ACT CAT GTG TGT ATA GAA GAA GGA GAA AAG CCC ATG
        1314        1324        1334        1344

Val Ile Leu Pro Tyr Met Asn Trp Gly Asn Leu Lys Leu Phe Leu
GTG ATA TTG CCT TAC ATG AAT TGG GGG AAT CTT AAA TTG TTT TTA
        1359        1369        1379        1389

Arg Gln Cys Lys Leu Val Glu Ala Asn Asn Pro Gln Ala Ile Ser
CGA CAG TGC AAG TTA GTA GAG GCC AAT AAT CCA CAG GCA ATT TCT
        1404        1414        1424        1434

Gln Gln Asp Leu Val His Met Ala Ile Gln Ile Ala Cys Gly Met
CAG CAA GAC CTC GTA CAC ATG GCT ATT CAG ATT GCC TGT GGA ATG
        1449        1459        1469        1479

Ser Tyr Leu Ala Arg Arg Glu Val Ile His Lys Asp Leu Ala Ala
AGC TAC CTG GCC AGA AGG GAA GTC ATC CAC AAA GAC CTG GCT GCC
        1494        1504        1514        1524

Arg Asn Cys Val Ile Asp Asp Thr Leu Gln Val Lys Ile Thr Asp
AGG AAC TGT GTC ATT GAT GAC ACA CTT CAA GTT AAG ATC ACA GAC
        1539        1549        1559        1569

Asn Ala Leu Ser Arg Asp Leu Phe Pro Met Asp Tyr His Cys Leu
AAT GCC CTC TCC AGA GAC TTG TTC CCC ATG GAC TAT CAC TGT CTG
        1584        1594        1604        1614

Gly Asp Asn Glu Asn Arg Pro Val Arg Trp Met Ala Leu Glu Ser
GGG GAC AAT GAA AAC AGG CCA GTT CGT TGG ATG GCT CTT GAA AGT
        1629        1639        1649        1659

Leu Val Asn Asn Glu Phe Ser Ser Ala Ser Asp Val Trp Ala Phe
CTG GTT AAT AAC GAG TTC TCT AGC GCT AGT GAT GTG TGG GCC TTT
        1674        1684        1694        1704

Gly Val Asn Ser Leu Trp Glu Leu Met Thr Leu Gly Gln Thr Pro
GGA GTG AAC AGC TTG TGG GAA CTC ATG ACT CTG GGC CAG ACT CCC
        1719        1729        1739        1749

Tyr Thr Leu Asp Ile Asp Pro Phe Glu Met Ala Ala Tyr Leu Lys
TAC ACG TTG GAC ATT GAC CCC TTC GAG ATG GCG GCA TAC CTG AAA
        1764        1774        1784        1794
```

FIG. 2B-4

```
Asp Gly Tyr Arg Ile Ala Gln Pro Ile Thr Cys Pro Asp Glu Leu
GAT GGT TAC CGA ATA GCC CAG CCA ATC ACC TGT CCT GAT GAA TTA
        1809        1819        1829        1839

Phe Ala Val Met Ala Cys Cys Trp Ala Leu Asp Pro Glu Glu Arg
TTT GCT GTG ATC GCC TGT TGC TGG GCC TTA GAT CCA GAG GAG AGG
        1854        1864        1874        1884

Pro Arg Phe Gln Gln Leu Val Gln Cys Leu Thr Glu Phe His Ala
CCC AGG TTT CAG CAG CTG GTA CAG TGC CTA ACA GAG TTT CAT GCA
        1899        1909        1919        1929

Ala Leu Gly Ala Tyr Val ***
GCC CTG GGG GCC TAC GTC TGA CTC CTC TCC AAT CCC ACA CCA TCA
        1944        1954        1964        1974
GGA AGA AGG TGC CTG TCG GGG CTC ACT TGA AGC CTG TCA GGG ATC
        1989        1999        2009        2019
CTT TGT ATA TCT AAC ACA ACG CCA ACA GAA GCA CAT TTG TCT TCC
        2034        2044        2054        2064
AGA ACA CCG TGC CTT AGA AAT GCT TTA GAA TCT GAA CTT TTT AAG
        2079        2089        2099        2109
ACA GAC TTA ATA ATG TGG CAT ATT TTC TAG ATA TCA CTT TTA TTA
        2124        2134        2144        2154
GGT TGA ACT GAA AGG GTT TTT GTA AAT TTT TTG GCC AAA ATT TTT
        2169        2179        2189        2199
TAA AAC ATA CTT ACT TTG GAC TAG GGG TAC ATT CTT ACA AAA TAA
        2214        2224        2234        2244
ATA AAC AGT TTT TAA AAT TGT TTA GAC ACA GAT ATT TGG AAT TAG
        2259        2269        2279        2289
CTA TCT TAG TGC CAA CTG CTT TTT ATT TTT TTA CTT CAT CAA GGT
        2304        2314        2324        2334
GAT GTA AGT GAC TTT GTT TAG ACA CAG ATA TTT GGA ATT AGC CTA
        2349        2359        2369        2379
TCT TAG TGC CAA CTG CTT TTT ATT TTT TTC CTT CAT CAA GGT GAT
        2394        2404        2414        2424
GTA AGT GAC TCA CCT TTA AAG TTT TTT TAG TGT TAT TTT TTA TCA
        2439        2449        2459        2469
CTA CTC TGG GAA ATG GTT TGT CTT CAA GAT GCA ATA CTT TTC TTA
        2484        2494        2504        2514
GTA AAG GAA AAA CAG CAT AAA AAG ATA CCT GGT CTG CCT TGT ACA
        2529        2539        2549        2559
AGA AAA CCG AAT ATT AGA GGA AGA AAA TTT AAA GAA AAG CTA GAG
        2574        2584        2594        2604
AAA AAA AAA ATT TTT TAA AAA ATA CTT ATT AGA AGC AAA CTG CCC
        2619        2629        2639        2649
TTG CAT GGA AAA CTG TTT ATT TTT TTC AGT GAA AAA GGA ATT CTG
        2664        2674        2684        2694
CTT TCG TGT TTT TGG GAA AGC AGG AAC TGA GTT CAT TAC ATC TTT
        2709        2719        2729        2739
```

FIG. 2B-5

```
AAT TTG GCA GAA ATT AGC CTT TCT GTG AAC CAG ATG TGG TTT GGG
              2754            2764            2774            2784
GCA GAT CTG TAG TAA ACA ATG GTG ATT TTA TTT ATT TTT ACT CTC
              2799            2809            2819            2829
TGG AAA AGG AGA TAA TAC AAT TCC AGA AAG TGA ACT CAT ATT TCT
              2844            2854            2864            2874
AAG GTA AGA TCC CTT TTA TGC ACC TAG AAT ATG CTA TGC ACA GAG
              2889            2899            2909            2919
CGG GTG CTT GAG TTG TTG TCG TTT TTT GTT TGT TTT TTA AAT GTA
              2934            2944            2954            2964
AAC TGG TAA ATT TTG TGC TTA TCT TCA AGG CTG GCT AAA GTA TAA
              2979            2989            2999            3009
AAT TGT TTT TTA AAC ACT TGA AAA ATT AAA GGA TTT GTT TTA TAT
              3024            3034            3044            3054
TAA AAA AAA AAA
              3067
```

FIG. 3A

```
CTCGGGCTGTGAGGGCTCGGGCCCCGGGCCCCGGGTGCCGGGGCCTCGGGGCCCCCCGG       -17
  30           40          50          60       TAAGCTTGATATCGAATTCCCGCCCCCGG
                                                          10          20
TGCTCGGGCGGGCC   Met Arg Ala Gly Arg Gly Val Pro Ser Gly              -2
  90      100    ATG CGC GCG GGC CGG GGC GTC CCG GGG AGC
                 110            120            130
Gly Leu Arg Ala Arg Arg Arg Arg Arg Cys Cys Cys Trp                   14
GGC CTG AGG GCC CGG CGG CGG CGG CGC TGC TGC TGC TGG
   140              150            160               180
Arg Met Leu Pro Pro Ala Ala Pro Val Pro Gly Pro Gly Arg Ala           29
CGG ATG CTG CCG CCC GCC GCC CCC GTC CCC GGC CCT GGC CGC GCT
       190            200            210            220
Pro Ala Gly Pro Ser Val Ser Leu Tyr Leu Ser Glu Asp Glu Val           44
CCT GCC GGA CCC AGC GTG AGC CTG TAC CTG AGC GAG GAC GAG GTG
         236            246            256             266
Arg Arg Leu Leu Gly Leu Asp Ala Glu Tyr Tyr Val Arg Asn               59
CGC CGG CTG CTT GGT CTT GAT GCA GAG TAC TAT GTG AGA AAT
         281            291            301             311
Asp Leu Ile Ser His Tyr Ala Leu Ser Phe Asn Leu Val Pro               64
GAC CTC ATC AGT CAC TAC GCT CTG TCC TTT AAC CTC GTG CCC
         326            336            346             356
Ser Glu Thr Asn Phe His Phe Thr Trp His Ala Lys Ser Lys               79
AGT GAG ACA AAC TTC CAC TTC ACT TGG CAT GCA AAG TCC AAG
         371            381            391             401
Val Glu Tyr Lys Leu Gly Phe Gln Val Asn Asn Phe Val Ala Met           94
GTT GAA TAT AAG CTG GGA TTC CAA GTG AAC AAC TTT GTG GCT ATG
         416  *   426         436            446
Gly Met Pro Gln Val Asn Ile Ser Ala Gln Gly Glu Gly Pro Arg          109
GGC ATG CCC CAG GTC AAT ATT TCT GCT CAA GGG GAG GGT CCA CGC
         461            471            481            491
Thr Leu Ser Val Phe Arg Val Glu Leu Ser Thr Gly Lys Val
ACT TTA TCA GTG TTT CGG GTC GAG CTT TCT TGT ACC GGC AAA GTC
         506            516            526            536
```

FIG. 3B

```
Asp Ser Glu Val Met Ile Leu Met Gln Leu Asn Leu Thr Val Asn       124
GAC TCT GAA GTC ATG ATT CTA ATG CAG CTC AAT CTG ACA GTG AAT
                            561            571*          581

Ser Ser Lys Asn Phe Val Leu Phe Asn Phe Lys Arg Arg Lys Met       139
TCC TCA AAA AAT TTT ACA GTT TTA AAT TTT AAA AGG AGG AAA ATG
                    606            616            626

Cys Tyr Lys Lys Leu Glu Glu Val Lys Thr Ser Ala Leu Asp Lys       154
TGC TAC AAA AAA CTT GAA GAA GTA AAA ACT TCA GCA TTG GAC AAA
            651            661            671

Asn Thr Ser Arg Thr Ile Tyr Asp Pro Val His Ala Ala Pro Thr       169
AAC ACT AGC AGA ACT ATT TAT GAC CCT GTC CAT GCA GCG CCA ACG
            686            696            706

Thr Thr Arg Val Phe Tyr Ile Ser Val Gly Val Cys Cys Ser Ala       184
ACT ACC CGT GTG TTT TAC ATC AGT GGG GTT TGC TCT GCA
            731            741            751            761

Val Ile Phe Leu Val Ala Ile Ile Leu Ala Val Leu His Leu His       199
GTG ATA TTT CTT GTA GCA ATA ATA TTA GCC GTT TTG CAC CTT CAT
            776            786            796            806▼

Ser Met Lys Arg Ile Glu Leu Asp Asp Ser Ile Ser Ala Ser Ser       214
AGC ATG AAA AGG ATT GAA CTG GAT GAC AGC ATC AGC GCC AGT
            821            831            841            851

Ser Ser Gln Gly Leu Ser Gln Pro Ser Thr Gln Thr Thr Gln Tyr       229
AGT TCC CAG GGG CTC TCT CAG CCG TCT ACC CAG ACG AGG TAT
            866            876            886            896▼

Leu Arg Ala Asp Thr Pro Asn Asn Ala Thr Pro Ile Thr Ser Ser       244
CTG AGA GCT GAC ACA CCC AAC AAT GCA CCT ATC ACC AGC TCC
            911            921            931            941

Ser Gly Tyr Pro Thr Leu Arg Ile Glu Ile Glu Lys Asn Asp Leu Arg Ser       259
TCA GGT TAT CCT ACC TTG CGG ATA GAG AAG AAC GAC TTG CGA AGT
            956            966            976            986

Val Thr Leu Leu Glu Ala Lys Ala Lys Val Lys Asp Ile Gly Ile       274
GTC ACT CTT CTG GAA GCC AAA GCC AAG GTG AAG GAT ATC GGA ATA
            1001           1011           1021           1031
```

FIG. 3C

```
Ser Arg Glu Arg Ile Thr Leu Lys Asp Val Leu Gln Glu Gly Ser    289
TCC AGA GAA AGG ATC ACA CTG AAA GAT GTC CTC CAA GAA GGT AGT
         1046         1056         1066         1076

Phe Gly Arg Ile Phe His Gly Ile Val Leu Val Asp Lys Arg Pro    304
TTT GGG CGT ATT TTC CAT GGG ATT GTA TTA GTA GAT AAA AGA CCA
         1091         1101 II      1111         1121

Asn Lys Glu Lys Gln Thr Phe Val Lys Thr Val Lys Asp Gln Ala    319
AAT AAA GAG AAG CAA ACA TTT GTA AAA ACA GTT AAA GAC CAA GCA
         1136         1146         1156 III     1166

Ser Glu Val Gln Val Thr Met Met Leu Thr Glu Thr Ser Cys Lys Leu  334
TCT GAA GTT CAG GTG ACG ATG ATG CTC ACC GAG AGC TGC AAG CTT
         1181     IV  1191         1201         1211

Arg Gly Leu His His Arg Asn Leu Pro Ile Thr His Val Cys        349

CGA GGT CTG CAC CAC AGA AAC CTC CCT ATT ACT CAT GTC TGC
         1226         1236         1246         1256

Ile Glu Gly Glu Gly Lys Pro Met Val Val Leu Pro Tyr Met Asn    364
ATA GAA GGA GAA GGG AAG CCC ATG GTG GTA TTG CCA TAC ATG AAT
    V    1271         1281         1291         1301

Trp Gly Asn Leu Lys Leu Phe Leu Arg Gln Cys Lys Leu Val Glu    379
TGG GGG AAT CTT AAA TTA TTT CTT CGG CAG TGC AAA TTA GTA GAA
         1316         1326         1336         1346

Ala Asn Asn Pro Gln Ala Ile Ser Gln Gln Asp Leu Val His Met    394
GCC AAT AAT CCA CAG GCA ATT TCC CAG CAA GAT CTG GTC CAT ATG
         1361     VIa 1371         1381         1391

Ala Ile Gln Ile Ala Cys Gly Met Ser Tyr Leu Ala Arg Arg Glu    419
GCT ATT CAG ATT GCC TGC GGG ATG AGC TAC CTG GCG AGG AGA GAA
         1406     VIb 1416         1426         1436

Val Ile His Arg Asp Leu Ala Ala Arg Asn Cys Val Ile Asp Asp    434
GTG ATC CAT AGA GAC CTG GCT GCT AGG AAC TGT GTC ATC GAC GAC
         1451     VII 1461         1471         1481

Thr Leu Gln Val Lys Ile Thr Asp Asn Ala Leu Ser Arg Asp Leu    449
ACT CTT CAA GTC AAG ATC ACA GAC AAT GCC CTT TCC AGA GAC TTG
         1496         1506         1516         1526
```

```
Phe Pro Met Asp Tyr His Cys Leu Gly Asp Asn Glu Asn Arg Pro    464
TTT CCT ATG GAC TAC CAC TGC CTA GGG GAC AAC GAG AAC AGG CCA
   VIII 1541                 1551                1561              1571

Val Arg Trp Met Ala Leu Glu Ser Leu Val Asn Asn Glu Phe Ser    479
GTG AGA TGG ATG GCT CTG GAA AGT CTG GTT AAT AAT GAG TTC TCT
         1586          IX      1596                1606              1616

Ser Ala Ser Asp Val Trp Phe Ala Phe Gly Val Thr Leu Trp Glu Leu    494
AGT GCT AGT GAC GTG TGG TTT GCC TTT GGA GTG ACG CTG TGG GAG CTC
         1631                1641                1651              1661

Met Thr Leu Gly Gln Thr Pro Tyr Val Asp Ile Asp Pro Phe Glu    509
ATG ACT CTC GGC CAG ACG CCC TAC GTG GAC ATC GAC CCC TTT GAG
         1676                1686                1696              1706

Met Ala Ala Tyr Leu Lys Asp Gly Tyr Arg Ile Ala Gln Pro Ile    524
ATG GCC GCT TAC CTG AAA GAT GGT TAC CGA ATA GCC CAG CCA ATC
         1721                1731                1741        XI    1751

Asn Cys Pro Asp Glu Leu Phe Ala Val Met Ala Cys Cys Trp Ala    539
AAC TGC CCT GAT GAA CTG TTT GCT GTG ATG GCC TGT TGC TGG GCC
         1766                1776                1786              1796

Leu Asp Pro Glu Pro Lys Phe Gln Gln Leu Val Gln Cys    554
TTG GAC CCT GAG AGG CCT AAG TTC CAG CAG CTG GTC CAG TGC
         1811                1821                1831              1841

Leu Thr Glu Phe His Ala Ala Leu Gly Ala Tyr Val ***    566
CTC ACA GAG TTC CAC GCT GCC CTG GGA GCC TAC GTC TGA CTT CTC
         1856                1866                1876              1886

TCC CCA TGC CGC CAC TCA GAA GAA AGT GCC TGT CTG TCA CGG ATG
         1901                1911                1921              1931

CCC CTC GTG CAG CGC AGT CAG TGC AGG GGC ACA CTG TCT CCA GAT
         1946                1956                1966              1976

CAC CCA GCC TTA GCA GTG CTT CCA AAC CTC AGC TTT TAA CGA TGA
         1991                2001                2011              2021

AGT AAT AAC GCA GAG TGT TTT CTA GAG TCG ACG TGC AGG
         2036                2046                2056
```

FIG. 3D

```
                                                                                      HUMAN
                                                                                      MOUSE
Amino acids 42-606
of SEQ ID NO:20  42  .RAAARPRPP ELQSASAGPS VSLYLSEDEV RRLIGLDAEL YYVRNDLISH YALSFNLLVP  HUMAN
    SEQ ID NO: 9  1  MLPPAAPVP  GPGRAPAGPS VSLYLSEDEV RRLLGLDAEL YYVRNDLISH YALSFNLLVP  MOUSE 101  SETNFLHFTW HAKSKVEYKL GFQVDNVLAM DMPQVNISVQ GEVPRTLSVF RVELSCTGKV  HUMAN
                 60  SETNFLHFTW ********** GFQVNNFVAM GMPQVNISAQ GEGPRTLSVF RVELSCTGKV  MOUSE 161  DSEVMILMQL NLTVNSSKNF TVLNFKRRKM CYKKLEEVKT SALDKNTSRT IYDPVHAAPT  HUMAN
                120  DSEVMILMQL NLTVNSSKNF TVLNFKRRKM CYKKLEEVKT SALDKNTSRT IYDPVHAAPT  MOUSE 221  TSTRVFYISV GVCCAVIFLV AILLAVLHLH NMKRIELDDS ISASSSSQGL SQPSTQTTQY  HUMAN
                180  TSTRVFYISV GVCCAVIFLV AILLAVLHLH SMKRIELDDS ISASSSSQGL SQPSTQTTQY  MOUSE 281  LRADTPNNAT PITS...YPT LRIEKNDLRS VTLLEAKGKV KDIAISRERI TLKDVLQEGT  HUMAN
                240  LRADTPNNAT PITSSSGYPT LRIEKNDLRS VTLLEAKAKV KDIGISRERI TLKDVLQEGS  MOUSE 338  FGRIFHGILI DEKDPNKEKQ AFVKTVKDQA SEIQVTMMLT ESCKLRGLHH RNLLPITHVC  HUMAN
                300  FGRIFHGILV DEKRPNKEKQ TFVKTVKDQA SEVQVTMMLT ESCKLRGLHH RNLLPITHVC  MOUSE
```

FIG. 4A

```
398  IEEGEKPMVI LPYMNWGNLK LFLRQCKLVE ANNPQAISQQ DLVHMAIQIA CGMSYLARRE  HUMAN
     ********** ********** ********** ********** ********** **********
360  IEEGEKPMVV LPYMNWGNLK LFLRQCKLVE ANNPQAISQQ DLVHMAIQIA CGMSYLARRE  MOUSE

458  VIHKDLAARN CVIDDTLQVK ITDNALSRDL FPMDYHCLGD NENRPVRWMA LESLVNNEFS  HUMAN
     *** ****** ********** ********** ********** ********** **********
420  VIHRDLAARN CVIDDTLQVK ITDNALSRDL FPMDYHCLGD NENRPVRWMA LESLVNNEFS  MOUSE

518  SASDVWAFGV NSLWELMTLG QTPYTLDIDP FEMAAYLKDG YRIAQPITCP DELFAVMACC  HUMAN
     ********** |******** **** |**** ********** ******* ** **********
480  SASDVWAFGV .TLWELMTLG QTPY.VDIDP FEMAAYLKDG YRIAQPINCP DELFAVMACC  MOUSE

578  WALDPEERPR FQQLVQCLTE FHAALGAYVX  606  HUMAN
     ********** | ********* **********
538  WALDPEERPK FQQLVQCLTE FHAALGAYVX  566  MOUSE
```

FIG. 4B

RECEPTOR-TYPE TYROSINE KINASE-LIKE MOLECULES

FIELD OF INVENTION

The present invention relates to proteins having receptor-type tyrosine kinase-like properties hinch represent a novel family of proteins related to protein tyrosine kinases. The present invention relates to the full length proteins and to subunits, mutants, derivatives and/or analogues thereof and to nucleotide sequences encoding same. The present invention also extends to ligands for the above proteins and to pharmaceutical compositions comprising the proteins and/or mutants, derivatives and/or analogues thereof and/or ligands thereto.

BACKGROUND OF THE INVENTION

The phosphorylation of tyrosine residues on protein substrates is a pathway whereby signals of grow the and differentiation are transmitted by growth factor receptors and transforming onoogenes (1). Evidence for this role of tyrosine phosphorylation came from the identification of receptors which bind known soluble growth factors. For example, the receptors for epidermal growth factor (EGF) (2), platelet derived growth factor (PDGF) (3) and colony stimulating factor-1 (CSF-1) (4) were all shown to be transmembrane molecules with the cytoplasmic regions defining a tyrosine kinase catalytic domain (5).

The other line of evidence for a critical role played by tyrosine phosphorylation in growth control came from the study of viral oncogenes (6–7). The sequences were shown to be directly involved in growth dysregulation by observations of a change in cell growth following introduction of DNA encoding these genes into fibroblasts. All ono genes have been shown to have close cellular homologues (proto-oncogenes). One of the first identified oncogenes was v-src, the cellular homologue (c-src) is the prototypical representative of the family of cytoplasmic tyrosine kinases which, following myristylation, become associated with the inner leaf of the cell membrane (8).

Protein-tyrosine kinases (PTKs) represent a family of phosphotransferases related by their conserved catalytic domains (reviewed in 7 and 25). Phylogenetic analysis of this family suggests that several subfamilies of the PTKs exist based on the organisation of their non-catalytic sequences. These families include i) The Src related PTKs such as c-yes, c-lyn and hck; ii) the JAK family, and iii) at least seven subfamilies of growth factor receptors.

In particular, these previously known PTKs contain the Rossman motif (32) which is putatively associated with ATP binding. The Rossman motif has three invariant glycine residues in a six amino acid cluster as follows: (SEQ ID NO:1) Gly-X-Gly-X-X-Gly, where X is an amino acid residue.

In accordance with the present invention, proteins having receptor-type PTK-like properties have been discovered representing a new family of proteins related to receptor-type PTKs but exhibiting one or more of the following characteristics: and/or an altered Rossman motif, a unique tri-amino acid sequence in the kinase catalytic domain and/or an extracellular region comprising leucine rich regions. The proteins having the receptor-type PTK-like properties of the present invention are designated herein "RYK" for "related to tyrosine kinases".

SUMMARY OF THE INVENTION

One aspect of the present invention is directed to an isolated protein having receptor-type protein tyrosine kinase (PTK)-like properties including ATP binding, wherein said protein has an Ala binding site comprising a sequence of amino acid residues with the proviso that said amino acid sequence is not Gly-X-Gly-X-X-Gly, where X is any amino acid residue, or a subunit, fragment, derivative or analogue of said protein.

More particularly, the present invention provides an isolated protein having PTK-like properties including ATP binding wherein said protein has an ATP binding site consisting of (SEQ ID NO:2) Gln-a-Gly-b-c-Gly, where a, b and c may be the same or different and each is an amino acid residue, or a subunit, fragment, derivative or analogue of said protein.

Another aspect of the present invention provides an isolated protein having PTK-like properties including ATP binding wherein said protein has an ATP binding site consisting of (SEQ ID NO:3) Gln-Glu-Gly-b-Phe-Gly, wherein b is Ser or Thr, or a subunit, fragment, derivative or analogue of said protein.

Still another aspect of the present invention relates to a protein having-PTK-like properties including a kinase catalytic domain which contains amino acid sequence Asp-Asn-Ala or a subunit, fragment, derivative or analogue of said protein. More particularly, the protein has a kinase catalytic domain with amino acid sequence Asp-Asn-Ala in motif VII of said domain.

Yet still another aspect of the invention is directed to an isolated protein having PTK-like properties including an extracellular domain wherein said protein contains at least two leucine rich regions in said extracellular domain, or a subunit, fragment, derivative or analogue of said protein.

Figure 1A:
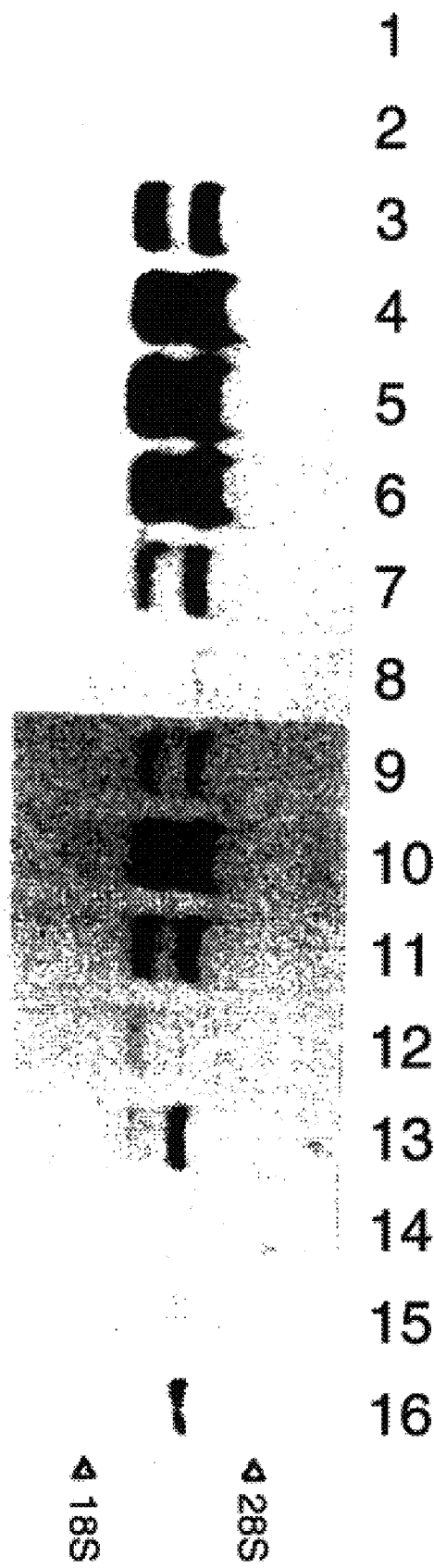
FIG. 1 is a photographic representation depicting an analysis of mouse and human RYK expression by Northern blotting. PolyA+mRNA (1 $\mu$g) from mouse tissues and in vitro cell lines was electrophoresed on a denaturing 1.0% w/v agarose/formaldehyde gel and the RNA transferred to Genescreen (Dupont). The transferred RNA was hybridized with either a 1.3 kb mouse RYK $^{32}$P-labelled probe and the filter autoradiographed for 16 hours at −70° C. The relative mobilities of 28S rRNA and 18S rRNA are indicated.

A. The tracks from the left to right are as follows: lane 1, human breast carcinoma cell line A431; lane 2, human erythroleukaemic cell line K562; lane 3, NIH-3T3 fibroblasts; and the following mouse tissues: lane 4, 13 day old embryo; lane 5, placenta; lane 6, ovary; lane 7, testes; lane 8, thymus; lane 9, liver; lane 10, lung; lane 11, kidney; lane 12, spleen; lane 13, brain; lane 14, salivary gland; lane 15, heart; lane 16, skeletal muscle.

B. The tracks from left to right are as follows lane 1, mouse mast cell line NFS60; lane 2, myelomonocytic cell line WEH13D-; lane 3, mouse mast cell line 32D; lane 4, mouse myeloid cell line B6SUTA; lane 5, mouse fibroblast cell line NIH-3T3; lane 6, mouse T cell line LB3; lane 7 and 8, myelomonocytic cell line WEHI3D +, lane 9, myelomonocytic cell line FDCP-1.

C. The tracks from left to right are as follows lane 1, plasma cell line PC13; lane 2, mouse embryonic cell line E30; lane 3, mouse embryonic cell line LE28; lane 4, mouse embryonic cell line LD3.3; lane 5, mouse embryonic cell-line P19; and, lane 6, mouse embryonic cell line D3.

Figure 2A:
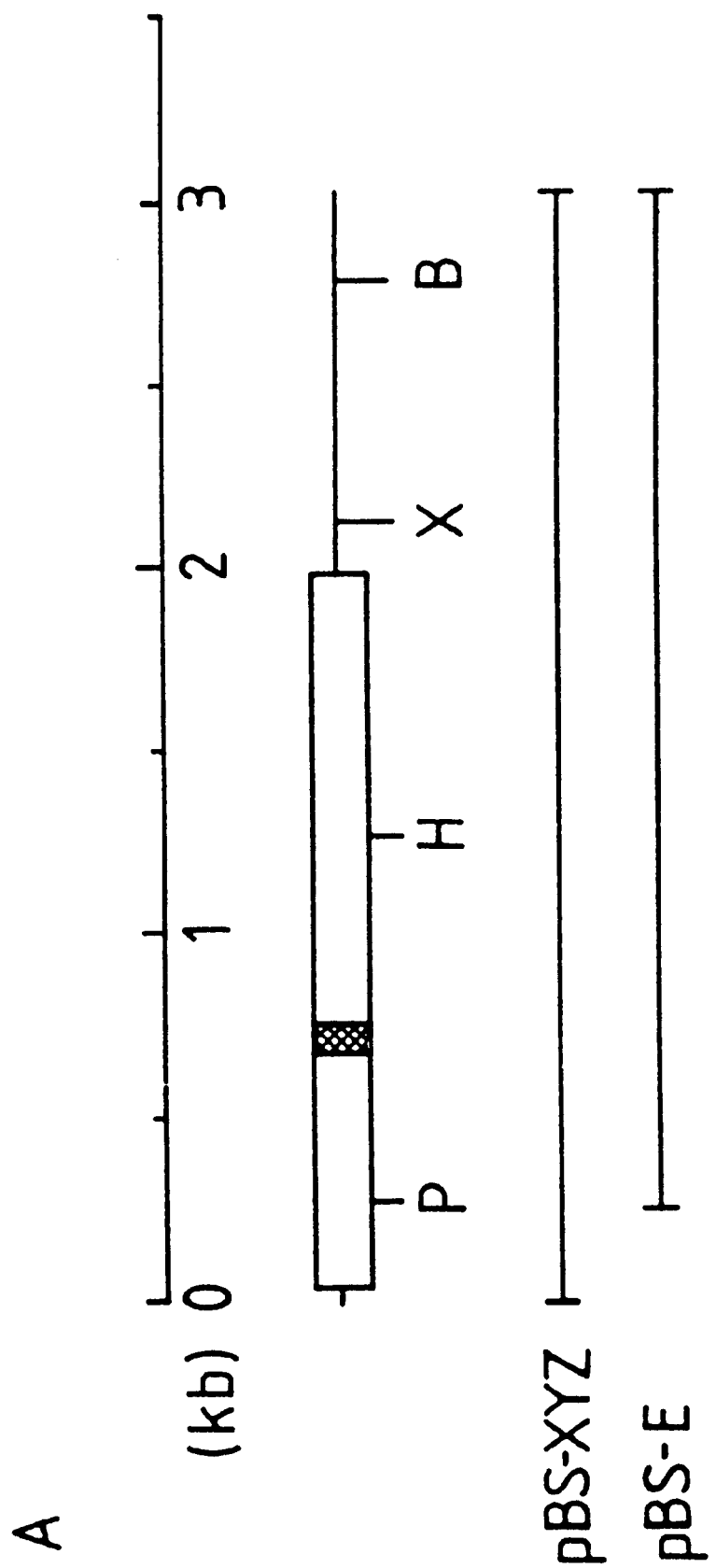
Figure 2B:
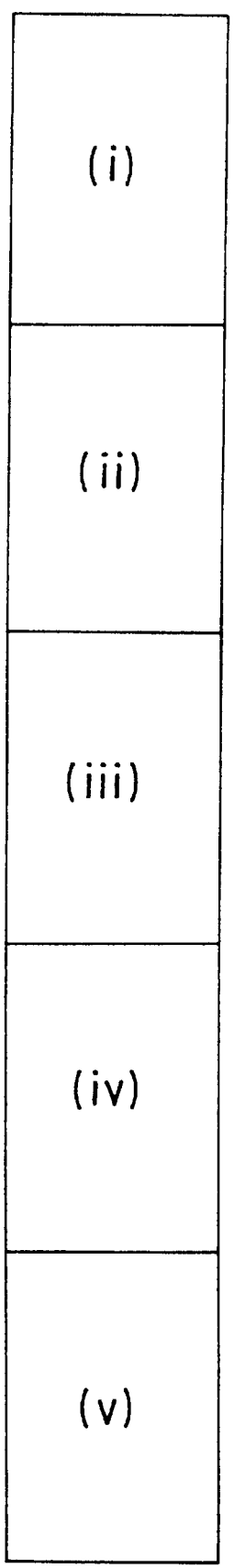

FIG. 2 shows the nucleotide and predicted amino acid sequence of the full length human RYK cDNA FIG. 2(A) Schematic representation and partial restriction map of the human RYK cDNA represented by clones pBS-XYZ and pBS-E. The open rectangle represents the coding region of 1896 bp, the thin line represents the 3' and 5' untranslated regions and the transmembrane domain is a shaded box. The following restriction sites are indicated: Bgl II FIG. 2(B), Hind III (H), Pst I (P) and Xba I (X). (B) Nucleotide SEQ. ID. NO. 7 and predicted amino acid sequence SEQ. ID. NO. 20 of the human RYK cDNA clone compiled from the sequences of pBS-XYZ and pBS-E. The DNA sequence is numbered from the polylinker region of a 3.067 kb clone in the vector pBluescript Nucleotides numbered from 1 to 18 are the pBluescript polylinker, nucleotides thereafter represent sequence of the clones. Deduced amino acid sequence is represented by the single letter amino acid code and is found above the nucleotide sequence. The putative initiation codon is an ATG (M) at amino acid position 1 and nucleotide position 132–134. The putative transmembrane domain is underlined, cysteine residues are circled and potential N-linked glycosylation sites (Asn-X-Ser/Thr) are indicated by an inverted bracket. Key residues of the catalytic domain are indicated in bold lettering. Two leucine-rich repeats are present in the human sequence, these are L1 SEQ ID NO: 4 (Leu-Ile-Gly-Leu-Asp-Ala-Glu-Leu-Tyr-Tyr-Val-Arg-Asn-Asp-Leu-Ile-Ser-His-Tyr-Ala-Leu-Ser-Phe) and L2 SEQ ID NO. 5 (Leu-Met-Gln-Leu-Asn-Leu-Thr-Val-Asn-Ser-Ser-Lys-Asn-Phe-Thr-Val-Leu-Asn-Phe-Lys-Arg-Arg-Lys). An in frame termination codon is found at nucleotide position 1962.

Figure 3:
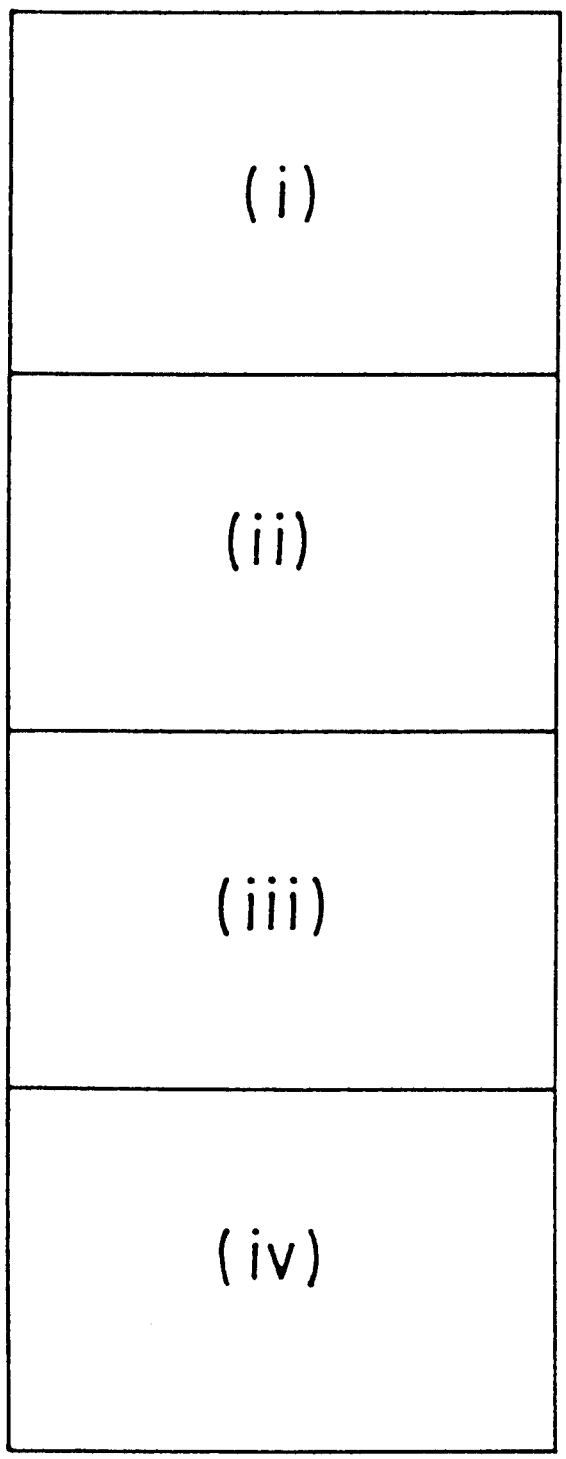

FIG. 3 is a representation of the nucleotide and predicted amino acid sequences of the mouse RYK cDNA clone SEQ. ID. NO. 8. The putative initiation methionine (ATG) is located at position 1 and is immediately followed by a signal peptide sequence which is underlined. The transmembrane domain is boxed and extends from residues 184 to 211. In the cytoplasmic domain, the subdomains of the conserved PTKs are indicated under the sequence by Roman numerals (I–XI). Important residues of the cytoplasmic domain are boxed, the ATP binding site SEQ. ID. NO:6 (Gln-Glu-Gly-Ser-Phe-Gly), conserved motif of PTK SEQ ID NO:7 (Asp-Leu-Ala-Ala-Arg-Asn), conserved motif of RTK SEQ ID NO: 1 (Trp-Met-Ala-Leu-Glu) and the novel motif (Asp-Asn-Ala). Putative N-linked glycosylation sites are indicated with a parenthesis. Cysteine residues are circled. The single letter amino acid code has been used throughout this diagram.

Figure 4:
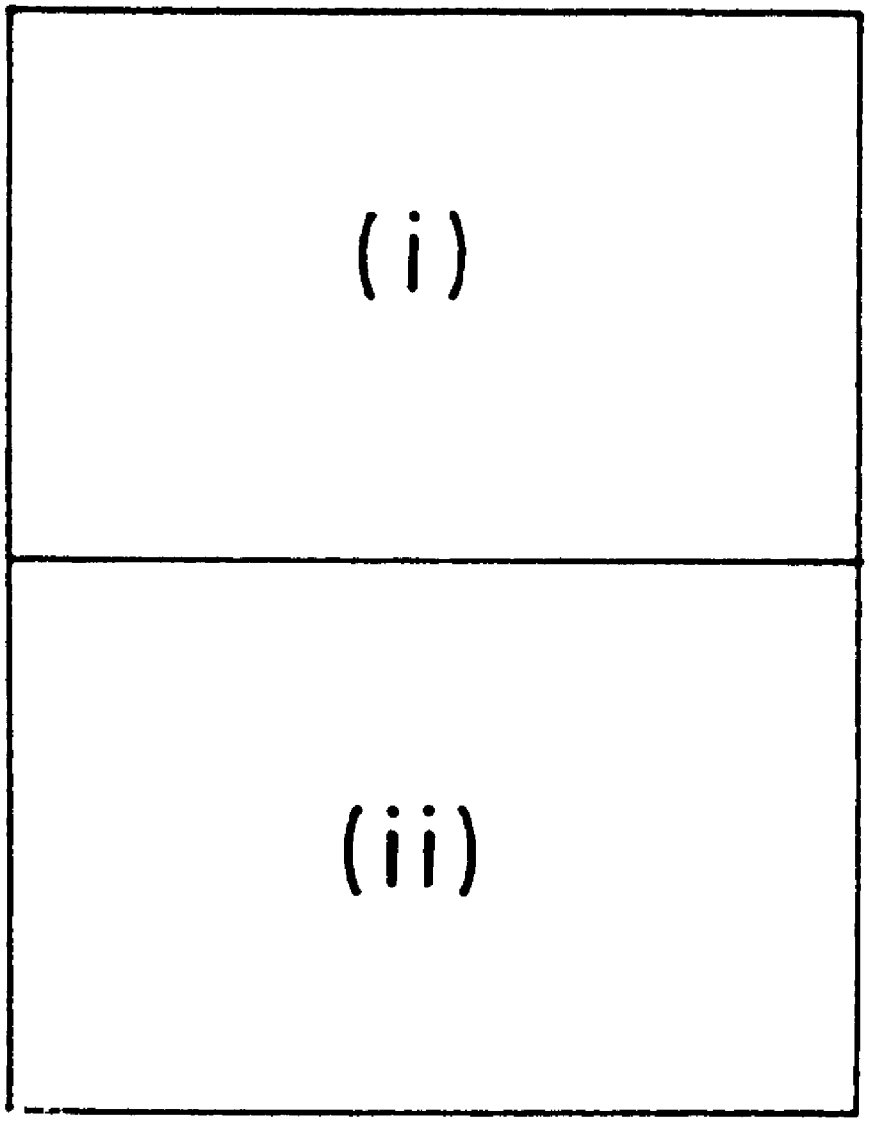

FIG. 4 shows a comparison of the deduced amino acid sequences of human and mouse RYK SEQ. ID. NO. 9. The amino acid sequences of human (42–606) (amino acids 42–606 of SEQ ID NO:20) and mouse RYK (1–566) were aligned and gaps (".") have been introduced to achieve maximum identity. Matches are indicated by an asterisk between the sequences and conservative amino acid substitutions by a vertical line. The single letter amino acid code has been used for this figure. "X" denotes an inframe stop codon. The putative transmembrane domain is underlined and the borders of the kinase domain indicated by square brackets.

Figure 5:
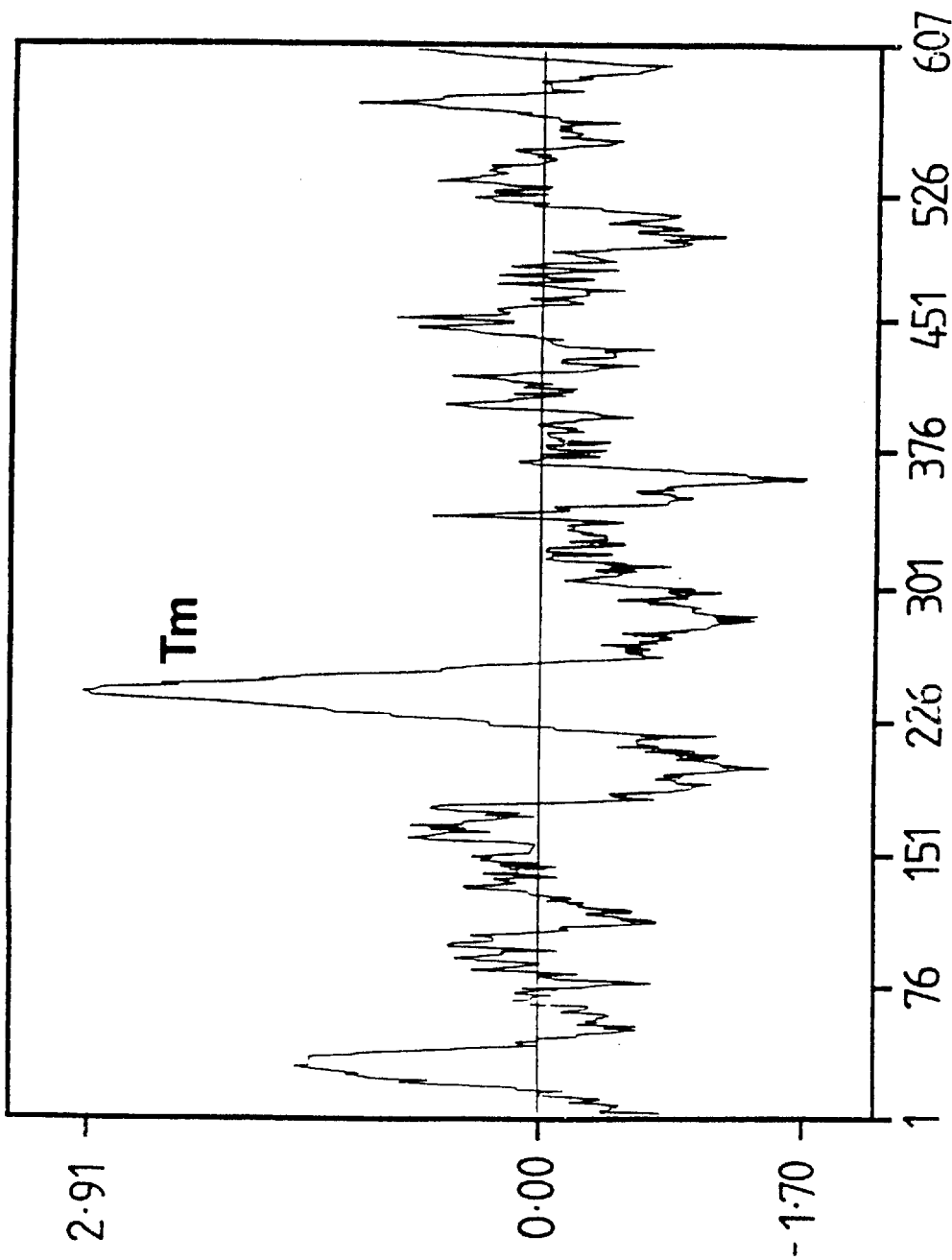

FIG. 5 shows a hydrophobicity plot of the predicted amino acid sequence of human RYK from FIG. 3B (amino acids 1–606) analysed by the hydrophilicity algorithm of Kyte and Doolittle (21), using a span length of 25 amino acids. The putative hydrophobic transmembrane domain is indicated (Tm).

Figure 6A:
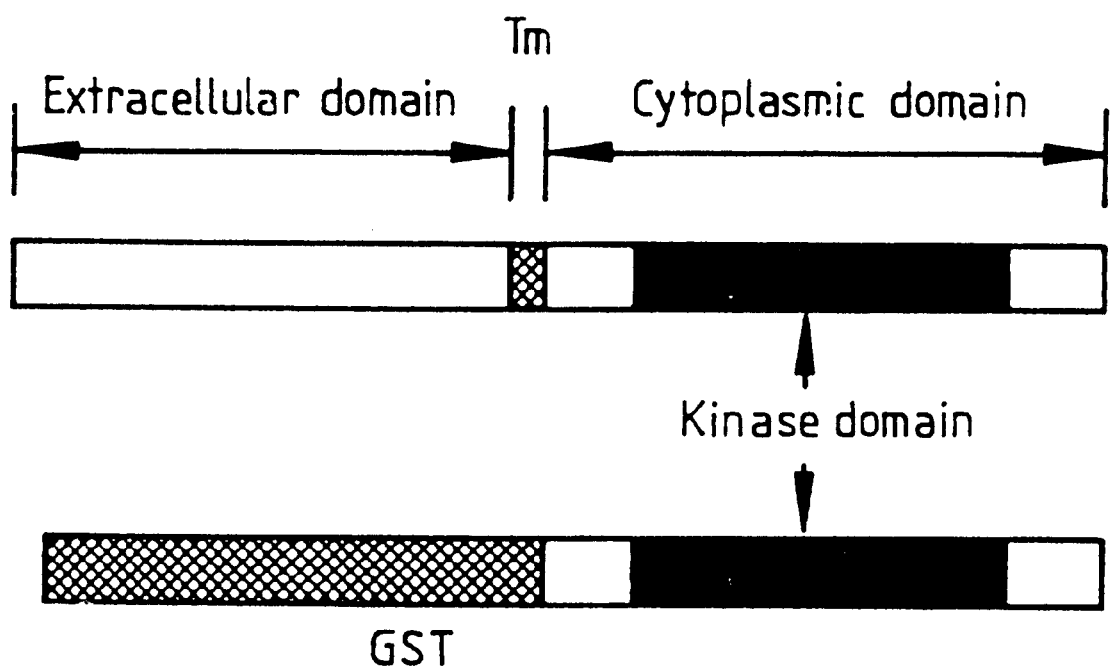
Figure 6B:
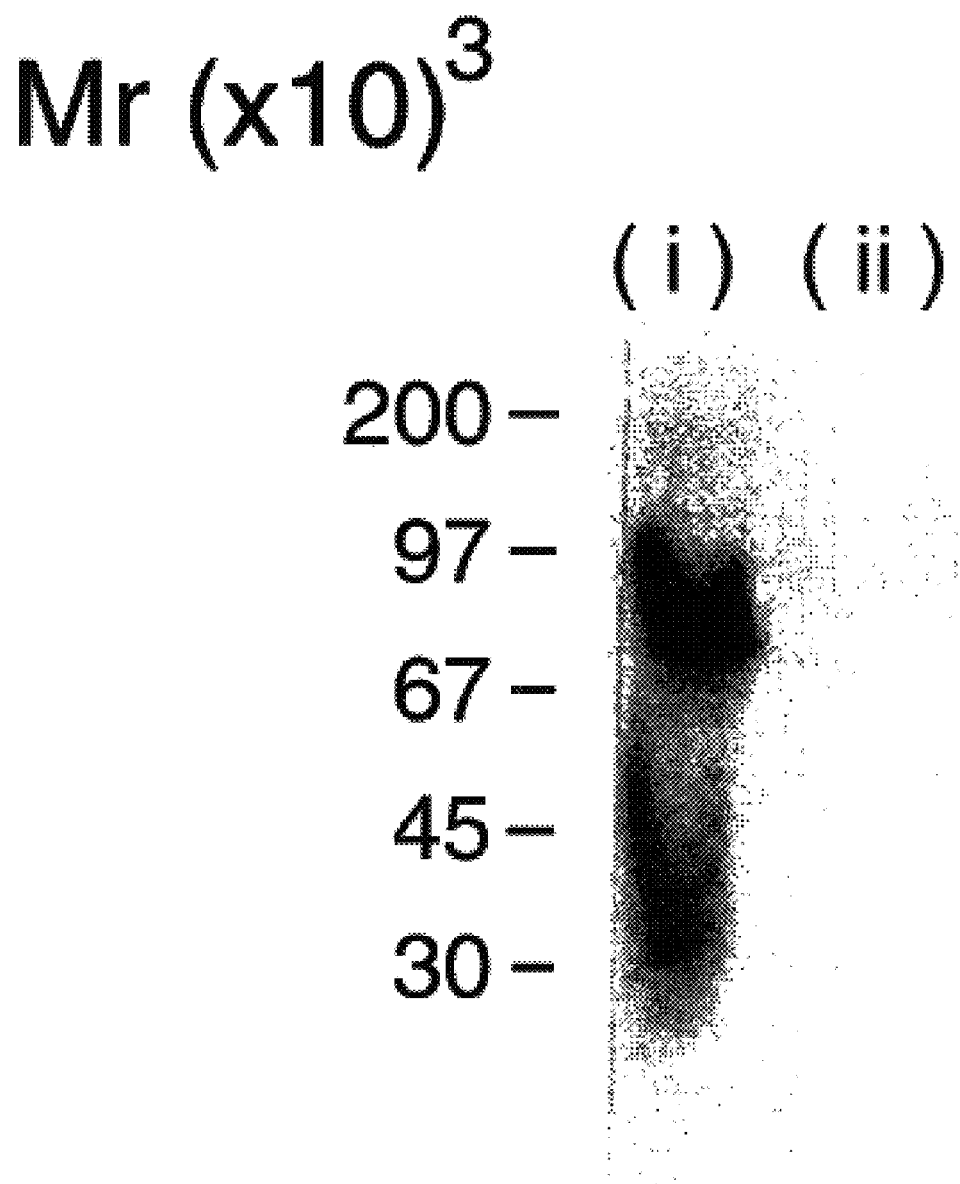

FIG. 6 is a schematic representation showing activity of the human RYK kinase domain
  A. Construction of the pGEX/RYK cytoplastic domain fusion proteins. Fusion proteins were generated between the cytoplastic domain of the human RYK molecule and glutathione-S-transferase, in the pGEX-3X vector. The upper diagram represents the intact human RYK protein the lower the fusion protein. The stiped area represents the GST while the filled area is the catalytic domain of human RYK.
  B. Demonstration of kinase activity by the human RYK kinase domain. Fusion proteins containing the human RYK kinase domain were constructed as described in Example 1 and expressed in bacteria and induced with IPTG. Bacteria were lysed in a Tx-100 lysis buffer and the solubilised proteins precipitated using glutathione-Sepharose. These immunoprecipitates were then subjected to in vitro labelling with gamma $^{32}$p-ATP in the presence of kinase buffer. Labelled material was eluted from the beads using SDS sample buffer under reducing conditions and electrophoresed on an 8% w/v SDS-polyacrylamide gel. The two lanes are immunoprecipitates from bacteria which was either (i) induced with IPTG, or (ii) not induced. Relative molecular weight markers are indicated.

Figure 7:
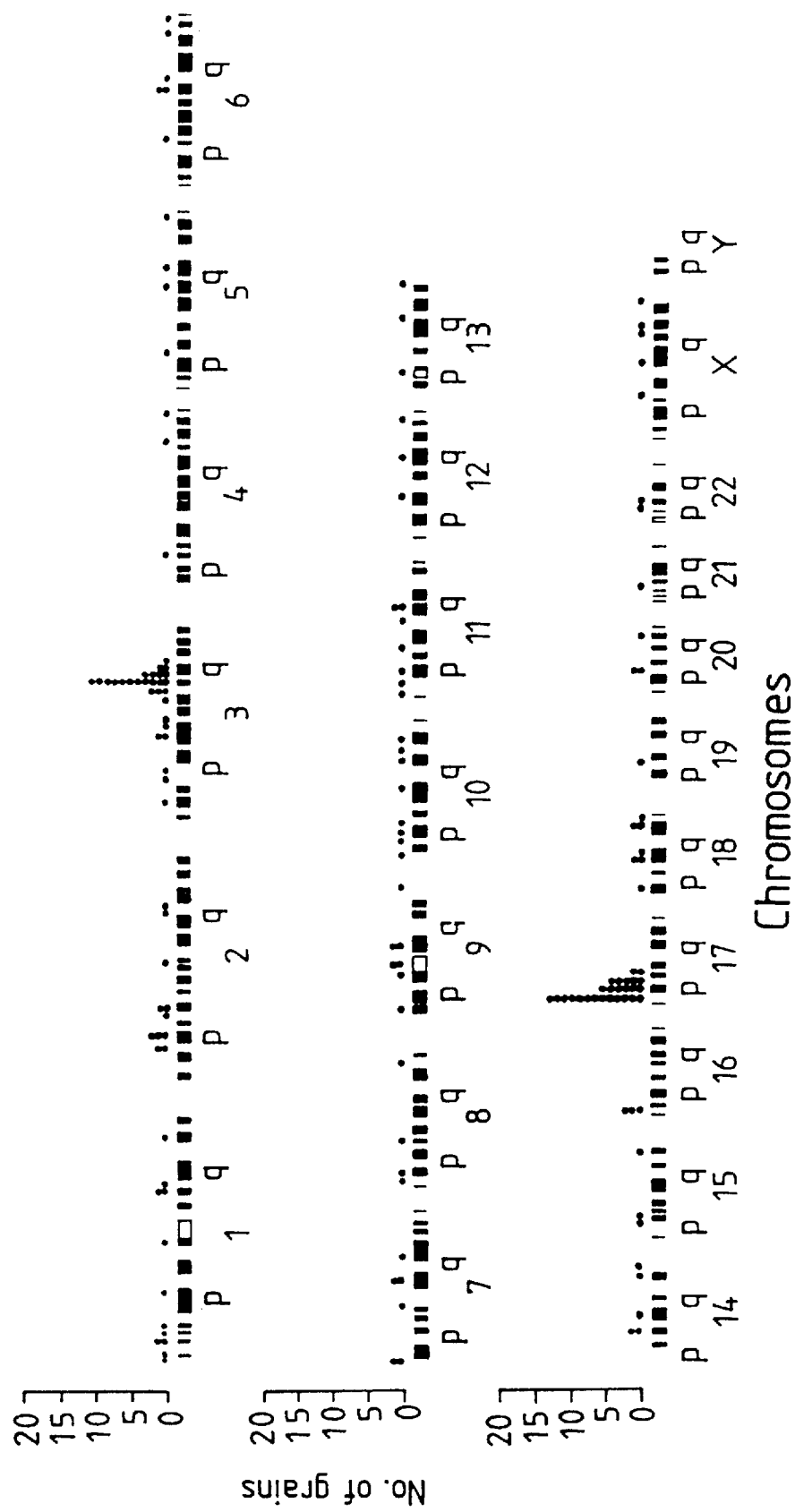

FIG. 7 is a representation of the localization of the human RYK gene on chromosomes from normal male lymphocytes using in situ hybridization. The ideogram represents the number of silver grains located on any chromosome within each metaphase.

Figure 8:
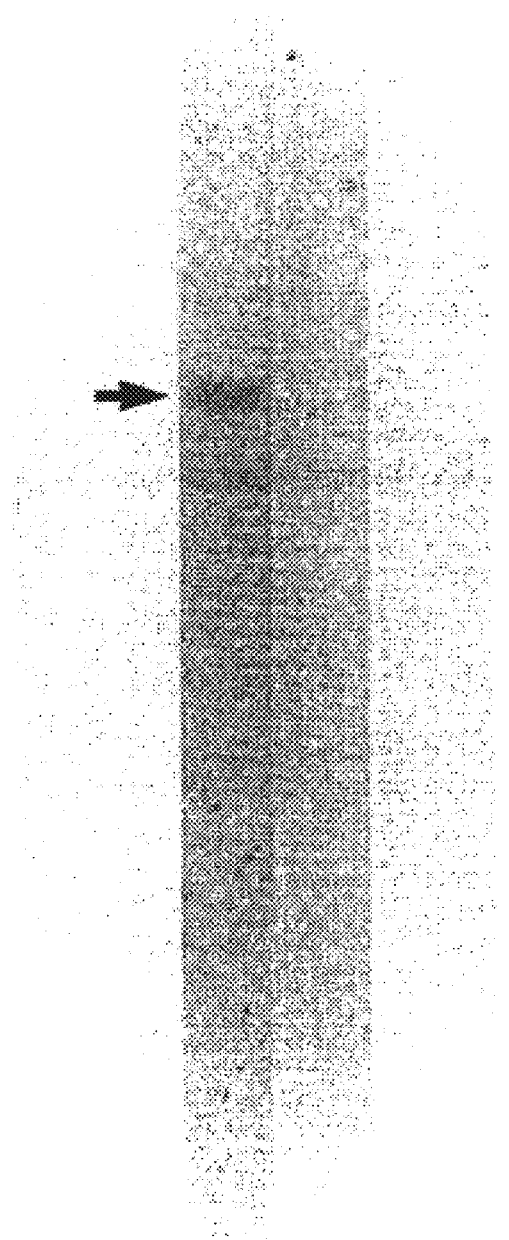

FIG. 8 shows an analysis of human RYK expression by Northern blotting. PolyA+ mRNA (0.5 μg) from in vitro cell lines MCF-7 (lane 1) and HSB-2 (lane 2) was electrophoresed on a denaturing 1.0% w/v agarose/formaldehyde gel and the RNA transferred to GeneScreen Plus (NEN). The transferred RNA was hybridised with a 2.3 kb human RYK $^{32}$P-labelled riboprobe and the filter autoradiographed for 16 hours at −70° C.

Figure 9A:
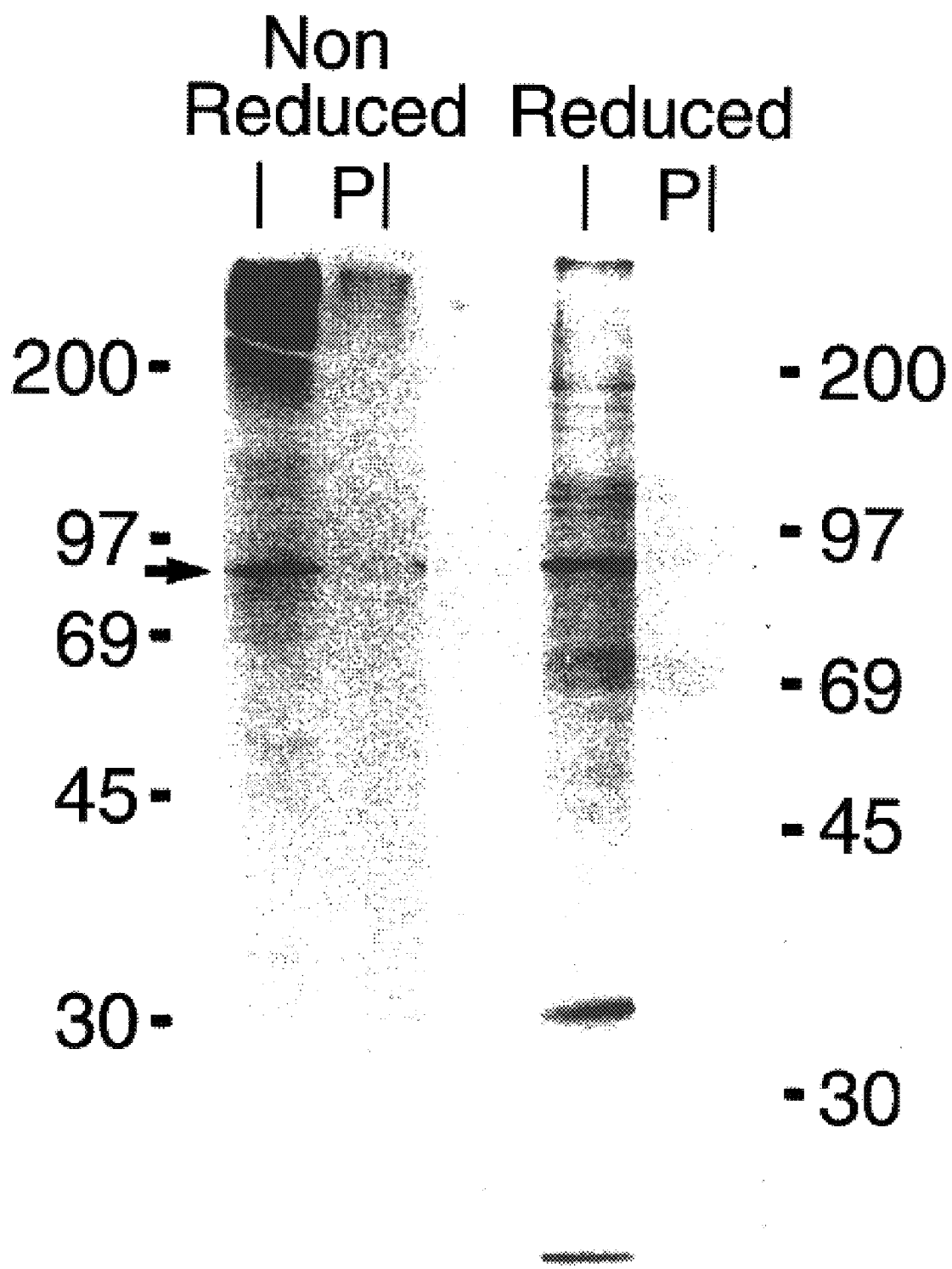

FIG. 9 shows SDS-PAGE analysis of RYK (A) Analysis of RYK immunoprecipitated from $^{35}$S-methionine labelled MCF-7 cells. Lysates of $^{35}$S-methionine labelled MCF-7 cells were immunoprecipitated with a rabbit anti-RYK sera (I; immune) or with pre-immune rabbit sera (PI; pre-immune) and analysed under reducing or non-reducing conditions as indicated (see Example 1). Gels were dried and autoradiographed for 24 hours. Molecular weight markers are indicated. (B) SDS-PAGE analysis of in vitro transcription/translation products derived using T7 RNA polymerase and the techniques described in Example 1. An aliquot of the total reaction volume (10 μl of 75 μl) was diluted in 10 μl of 2× SDS-PAGE sample buffer containing 2% v/v beta-mercaptoethanol, boiled and loaded onto an 8% w/v denaturing acrylamide gel. The dried gel was exposed for 2 hours on a phosphorimager cassette (Molecular Dynamics). The following templates were used: pCDM8 (lane 1), pCD.Human.RYK (lane 2), pCD.Mouse.RYK (lane 3) and pCD.Mouse.NYK (lane 4). Molecular weight markers are indicated.

DETAILED DESCRIPTION OF PREFERRED EMBODIMENTS

The present invention is directed to proteins including polypeptides having receptor-type PTK-like properties in isolated, recombinant and/or synthetic form including subunits, mutants, derivatives and analogues thereof. The proteins of the present invention have "receptor-type PTKC-like properties" since by comparison to known receptor-type PTKs, they possess a signal peptide and extracellular, transmembrane and intracellular domains and have amino acid sequence homology to a kinase catalytic domain within the intracellular domain. By convention, the kinase catalytic domain is divided into motifs identified by Roman numerals I–XI.

However, the proteins of the present invention differ in one or more important respects thus defining a new family of tyrosine kinases. The differences are in one or more of the ATP binding site, motif VII of the Kinase catalytic domain and/or the extracellular region. For convenience, the proteins of the present invention having receptor-type PTK-like properties are referred to herein as "RYK". When reference is made to extracellular, transmembrane and intracellular domains, this applies whether or not the RYK molecule is in isolated, recombinant or synthetic form.

Preferably, the RYK is of human or murine origin. Preferably, the murine RYK is mouse RYK. However, the present invention extends to RYK homologues from non-human and non-murine sources such as livestock animals (e.g. sheep, goats, cows, horses or pigs), companion animals (e.g. cats or dogs), laboratory test animals (e.g. rabbits or guinea pigs) and captive and free wild animals. The present invention also encompasses peptide and polypeptide fragments derived from the above mentioned RYK proteins including subunits, mutants, derivatives or analogues thereto.

The RYK molecule of the present invention comprises an amino acid sequence with an ATP binding site which is not Gly-X-Gly-X-X-Gly (Rossman motif) (SEQ ID NO.1) wherein X is any amino acid residue. More particularly, the ATP binding site is defined by the amino acid sequence Gln-a-Gly-b-c-Gly (SEQ. ID. NO. 2) where a, b and c may be the same or different and each is an amino acid residue. Preferably, the amino acid sequence is Gln-Glu-Gly-b-Phe-Gly (SEQ. ID. NO. 3) where b is Ser or Thr. The term "ATP binding site" includes a putative ATP binding site such as when determined by amino acid sequence similarity rather than direct ATP binding data.

The present invention extends to a portion of the RYK molecule without an ATP binding site or putative ATP binding site provided that in its full length or near full length form, the molecule comprises an ATP binding site as defined above.

Advantageously, the mammalian RYK is a biologically pure or isolated preparation meaning that it has undergone some purification away from other proteins and/or non-proteinacous material. The purity of the preparation may be represented as at least 40% RYK, preferably at least 60% RYK, more preferably at least 75% RYK, even more preferably at least 85% RYK and still more preferably at least 95% RYK relative to non-RYK material as determined byweight, activity, amino acid similarity, antibody reactivity or other convenient means.

The mammalian RYK of the present invention may be naturally occurring or may be synthetic meaning that it is prepared by recombinant DNA or chemical synthetic techniques. In any event, the present invention encompasses RYK molecules having the naturally occurring amino acid sequence as well as molecules having single or multiple amino acid substitutions, deletions and/or additions.

Amino acid insertional derivatives of the mammalian RYK of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. beletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where mammalian RYK is derivatised by amino acid substitution, the amino acids are generally replaced by other amino acids having like properties such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield synthesis) and the like, or by recombinant DNA manipulations. Techniques for making substitution mutations at predetermined sites in DNA having known or partially known sequence are well known and include, for example, oligonucleotide directed mutagenesis. The manipulation of DNA sequence to produce variant proteins which manifest as substitutional, insertional or deletional variants are conveniently elsewhere described (for example see Sambrook et al. (11)).

Other examples of recombinant or synthetic mutants and derivatives of the mammalian RYK of the present invention include single or multiple substitutions, deletions and/or additions of any molecule naturally or artificially associated with the molecule such as carbohydrates, lipids and/or proteins or polypeptides. For example, different glycosylation patterns or elimination of glycosylation can result from expressing the mammalian RYK in different host cells. It should be noted that reference herein to "mammalian RYK" includes RYK produced by recombinant means in bacteria or in animals cells or produced by chemical synthetic menas. Accordingly, "mammalian RYK" is a RYK of mammalian origin but not necessarily produced in mammalian cells.

Particularly useful mutants include truncated mutants, i.e. RYK molecule absent N-terminal and/or C-terminal portions conveniently made using cDNA molecules truncated at the 5' and/or 3' ends, respectively. Furthermore, the present invention extends to subunits or fragments of mammalian RYK carrying one or more of the extracellular domain, transmembrane domain and/or cytoplasmic domain (also referred to as kinase catalytic domain or intracellular domain). A subunit or fragment containing the extracellular domain is particularly useful for screening for ligands of RYK or antagonists to RYK-ligand binding or may be useful as an antagonist itself. Accordingly, the present invention extends to a subunit or fragment of mammalian RYK containing the extracellular domain or portion or derivative thereof. By "subunit" or "fragment" is meant a non-fun length RYK molecule. Preferably, the subunit or fragment is the extracellular domain portion of RYK. More particularly, the present invention extends to an isolated extracellular domain or part or derivative thereof, said domain characterised in that it is isolatable from mammalian RYK and comprises at least one leucine rich region. Preferably, the mammalian RYK is human RYK. Preferably, the extracellular domain comprises at least two leucine rich regions. Preferably, the leucine rich regions comprise the amino acid sequences:

Leu-Ile-Gly-Leu-Asp-Ala-Glu-Leu-Tyr-Tyr-Val-Arg-Asn-Asp-Leu-Ile-Ser-His-Tyr-Ala-Leu-Ser-Phe (SEQ. ID. NO. 4); and/or Leu-Met-Gln-Leu-Asn-Leu-Thr-Val-Asn-Ser-Ser-Lys-Asn-Phe-Thr-Val-Leu-Asn-Phe-Lys-Arg-Arg-Lys (SEQ. ID. NO:5), or have at least 70–80% amino acid similarity thereto.

Other useful mutants include hybrid molecules and fusion molecules. A hybrid RYK molecule includes a molecule with at least part of one domain from a RYK from a first species of mammal fused or otherwise associated with at least part of another domain from a RYK from a second different species of mammal. For example, the extracellular domain or part thereof of human RYK may be fused or associated with other domains of mouse RYK. Alternatively, the RYK hybrid or fusion molecules may be with regions of growth factor receptors such as Epidermal Growth Factor Receptor (EGFR).

In a further alternative embodiment, the hybrid occurs within a single domain and hence, for example, the hybrid molecule may comprise a hybrid extracellular domain.

The present invention also extends to subunits, functional chemical equivalents or analogues of mammalian RYK herein described.

Analogues of the mammalian RYK protein contemplated herein include, but are not limited to, modifications to side chains, incorporation of unnatural amino acids and/or derivatising the molecule and the use of crosslinkers and other methods which impose conformational constraints on the molecule. Examples of side chain modifications contemplated by the present invention include modifications of amino groups such as by reductive alkleation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6 trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N hydroxysuccimide esters and hetero-bifunctional reagents which usually contain an amino-reactive moiety such as N-hydroxysuocinimide and another group specific-reactive moiety such as maleimido or dithio moiety or carbodiimide. In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of ccclic peptides or analogues by introducing covalent bonds such as forming an amide bond between the N and C termini, between two side chains or between a side chain and the N or C terminus.

The present invention also extends to subunits, fragments, derivatives, homologues, analogues and immunological, functional and/or structural relatives of the mammalian RYK contemplated herein. Accordingly, reference herein to mammalian RYK, RYK molecules or RYK-like molecules is to be taken as covering the full length molecule or any subunits, fragments, derivatives, analogues, homologues and/or relatives thereof. In its most preferred form, the RYK of the present invention is human RYK having an amino acid sequence substantially as set forth in FIG. 2B, or having similarity thereto such as in the order of at least 50–70%, preferably at least 80% and most preferably at least 90% to all or a region or part thereof or is mouse RYK having an amino acid sequence substantially set forth in FIG. 3 or having similarity thereto as defined above.

In a most preferred embodiment, the mammalian RYK of the present invention is human RYK and comprises a signal peptide, and extracellular, transmembrane and cytoplasmic (kinase) domains. The human RYK molecule is approximately 500–700 amino acids in length; preferably 550–650 amino acids in length, more preferably 590 to 620 amino acids in length and most preferably about 606 amino acids in length with a molecular weight of the unglycosylated form of about 60,000–72,000 daltons as determined by SDS-PAGE relative standard molecular weight markers. The glycosylated form of the molecule has a molecular weight in the range 70,000–120,000 as determined by SDS-PAGE relative standard molecular weight markers. The glycosylated form of the molecule includes both natural glycosylation patterns and altered glycosylation patterns.

The present invention extends to an isolated protein having RYK properties including a catalytic kinase domain or a putative catayltic kinase domain wherein said catalytic kinase domain contains amino acid sequence Asp-d-e wherein d and e may be the same or different and each is an amino acid residue. Preferably, d is Asn. Preferably, e is Ala. Most preferably, the sequence is Asp-Asn-Ala and the RYK protein is as hereinbefore defined or a subunit, fragment, derivative or analogue thereof.

Another aspect of the present invention provides an isolated protein having receptor-type PTK-like properties including an extracellular domain wherein said extracellular domain contains two leucine rich regions, or a subunit, fragment, derivative or analogue of said protein. Preferably, the leucine rich regions are:

Leu-Ile-Gly-Leu-Asp-Ala-Glu-Leu-Tyr-Tyr-Val-Arg-Asn-Asp-Leu-Ile-Ser-His-Tyr-Ala-Leu-Ser-Phe (SEQ. ID. NO. 4);

and/or

Leu-Met-Gln-Leu-Asn-Leu-Thr-Val-Asn-Ser-Ser-Lys-Asn-Phe-Thr-Val-Leu-Asn-Phe-Lys-Arg-Arg-Lys (SEQ. ID. NO. 5)

or having at least 70–80% amino acid similarity thereto.

Preferably, the protein is RYK as hereinbefore described or a subunit, fragment, derivative or analogue thereof.

Yet another aspect of the present invention contemplates an isolated protein having receptortpe PTK-like properties including ATP binding, a kinase catalytic domain and/or an extracellular domain wherein said protein has one or more and preferably at least two of the following characteristics:

i) it has an ATP binding site consisting of Gln-Glu-Gly-b-Phe-Gly, where b is Ser or Thr;

ii) it has a kinase catalytic domain which includes amino acid sequence Asp-Asn-Ala in motif VII of said kinase catalytic domain; and/or iii) it has an extracellular domain comprising two leucine rich repeats, or subunits, fragments or derivatives or analogues of said protein.

Preferably, the RYK protein is as hereinbefore defined including subunits, fragments, derivatives or analogues thereof.

The mammalian RYK of the present invention may be of normal cell origin or may be from a genetically modified cell such as, for example, tumour cells. Types of cells carrying the human RYK molecule include but are not limited to cells from one or more of the following sources: kidney, brain, placenta, ovary, lung, thymus and spleen. Most preferably, the RYK is from cytokine (e.g. IL-1) induced human hepatoma cells.

The present invention is also directed to nucleic acid molecules encoding mammalian such as human or mouse RYK including its fragments, derivatives, analogues, homologues and/or relatives. The nucleic acid molecules may be RNA or DNA (e.g. cDNA), single or double stranded, linear or a covalently closed circle. The nucleic acid molecules may also be genomic DNA. The nucleotide sequence may correspond to the naturally occurring sequence or may contain single or multiple nucleotide substitutions, deletions and/or additions. The nucleic acid molecules may also be part of a vector such as an expression and/or cloning vector and may contain extraneous nucleic acid material encoding a signal peptide, fusion peptide, purification peptide and/or marker peptide. The preferred nucleotide sequence is set forth in FIG. 2B (human) or FIG. 3 (mouse) and includes molecules having at least 50–70%, preferably at least 80% and most preferably at least 90% similarity to all or a region thereof.

The mammalian RYK and/or nucleic acid molecules encoding same of the present invention have important utility in modulating growth and differentiation of cells. Accordingly, the present invention extends to ligands for the mammalian RYK and in particular ligand(s) to human and mouse RYK and to any agonists and antagonists of RYK-ligand interaction.

Accordingly, another aspect of the present invention contemplates a method for identifying a ligand for mammalian RYK said method comprises labelling an extracellular portion of a RYK molecule with a reporter molecule and using said labelled molecule to screen a cDNA expression library. The labelled molecule may be a full length RYK molecule or may be a fragment or part thereof. The labelled molecule must still be able to bind or otherwise associate with a putative ligand.

In an alternative embodiment, a RYK extracellular domain is fused to a truncated growth factor receptor lacking its extracellular domain to form a hybrid molecule and then transfecting the hybrid molecule into a cell line dependent on that particular growth factor. The cell line is then contacted with a range of molecules including proteinaceous molecules and non-proteinaceous chemicals. Putative ligands are identified by screening for survival, maintenance or proliferation of said cell line. An example of a suitable growth factor is Epidermal Growth Factor (EGF).

Since the RYK or a genetically modified form thereof may be an oncogenic protein, antagonists to the RYK are of particular relevance. Such antagonists include antibodies (monoclonal or polydonal), the receptor itself in soluble form, specific peptides or proteins and/or carbohydrates amongst others (e.g. the fragments, derivatives, analogues, homologues and relatives of RYK as contemplated above). These types of antagonists are useful in developing anti-tumour agents where the growth or maintenance of the tumour itself is supported by the RYK of the present invention. Accordingly, the addition of an effective amount of an antagonist to the tumour-associated RYK will inhibit, reduce or otherwise interfere with RYK activity and thus prevent, reduce and/or inhibit tumour growth. The present invention, therefore, also extends to pharmaceutical compositions comprising one or more antagonists to RYK The present invention is particularly directed to the treatment of carcinomas and tumours in epithelial tissues and haemopoietic tumours and sarcomas.

In other circumstances, however, it may be useful to promote ligand-RYK binding and/or interaction. Accordingly, the present invention attends to agonists of RYK which facilitate ligand-RYK interaction and to pharmaceutical compositions comprising same.

Accordingly, the present invention contemplates a pharmaceutical composition comprising as active ingredient, RYK or fragments, parts or derivatives thereof, RYK fusion or hybrid molecules, RYK ligands, RYK-ligand antagonists and/or RYK-ligand agonists, depending on the condition to be treated. For example, a RYK-ligand antagonist or a RYK ligand may be useful as an anti-cancer agent such as for treatment of carcinomas. For convenience, and as a short hand notation for the following description of pharmaceutical compositions, all of the above molecules and referred to herein after as "active molecules". The use of the term "active molecule(s)" therefore should be read as one or more of the above molecules depending on the condition to be treated.

The active molecules of the pharmaceutical composition are contemplated to exhibit therapeutic activity when administered in an amount which depends on the particular case. The variation depends, for example, on the animal and the active molecule. For example, from about 0.05 μg to about 20 mg of RYK ligand or RYK-ligand antagonist may be administered per kilogram of body weight per day to disrupt RYK-ligand interaction. Dosage regimes may be adjusted to provide the optimum therapeutic response. For example, several divided doses may be administered daily, weekly, monthly or in other suitable time intervals or the dose may be proportionally reduced as indicated by the exigencies of the situation. The active molecules may be administered in a convenient manner such as by the oral, intravenous (where water soluble), intraperitoneal, intramuscular, subcutaneous, intranasal, intradermal or suppository routes or implanting (e.g. using slow release molecules). Depending on the route of administration, the active molecules may be required to be coated in a material to protect said molecules from the action of enzymes, acids and other natural conditions which may inactivate said ingredients. For example, a low lipophilicity of RYK or its ligands may allow these to be destroyed in the gastrointestinal tract by enzymes capable of cleaving peptide bonds and in the stomach by acid hydrolysis. Accordingly, in order to administer the pharmaceutical composition by other than parenteral administration, the active molecules may be coated by, or administered with, a material to prevent its inactivation.

The active molecules may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol phenol sorbic acid, thormerosal and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active molecules in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active molecules are suitably protected as described above, the pharmaceutical composition may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixrs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in the pharmaceutical compositions is such that a suitable dosage will be obtained. Preferred compositions or preparations according to the present invention are prepared, so that an oral dosage unit form contains between about 0.05 μg and 20 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active molecule, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, aqueous solutions, coatings, antibacterial and antifungal agents, isotonic and absorption delaying agents, and the like. The use of such media and agents for pharmaceutical compositions is well known in the art. Except insofar as any conventional media or agent is incompatible with the active ingredient, use thereof in the pharmaceutical compositions is contemplated. Supplementary active molecules can also be incorporated into the compositions.

Another aspect of the present invention contemplates a method of inhibiting, reducing or otherwise interfering with interaction between a protein having receptor-type PTK-like properties and a ligand thereof in a mammal said method comprising the administration of a ligand binding interfering effective amount of an antagonist to said ligand interaction for a time and under conditions sufficient to inhibit, reduce or otherwise interfere with said interaction. More particularly, the present invention contemplates a method of inhibiting, reducing or otherwise interfering with RYK-ligand interaction in a mammal said method comprising the administration of a RYK-ligand interfering effective amount of an antagonist to RYK-ligand interaction for a time and under conditions sufficient to inhibit, reduce or otherwise intefere with said interaction. Generally, such inhibition, reduction or interference will be useful in preventing, reducing and/or inhibiting tumour growth. Generally, the mammal is a human, mouse, livestock animal, laboratory test animal, captive or free wild animal. More particularly, the mammal is a human. The antagonist may be a chemical compound or polypeptide or protein. The antagonist may also be the ligand itself or the extracellular region of RYK. The tumour is generally a carcinoma or sarcoma or epithelial or haemopoietic tissue.

Yet another embodiment of the present invention extends to the use of RYK to phosphorylate tyrosine residues on a protein substrate. This will be useful for in vitro labelling.

Still yet another aspect of the present invention is directed to the use of mammalian RYK in the manufacture of a medicament for the treatment against cancer or tumour growth.

The present invention also extends to nucleic acid molecules in the form of oligonucleotide probes or primers useful for detecting genomic sequences encoding a mammalian RYK molecule and in particular human RYK. More particularly, the oligonucleotide probes will be specific to particular regions of the genomic sequence such as those sequences encoding the extracellular domain, transmembrane domain or intracellular domain (including kinase catalytic domain) of RYK. Even more particularly, the oligonucleotide probes will be useful in screening a genomic sequence for abnormalities in relation to the RYK coding sequence which result in an abnormal or mutant RYK which might in turn result in or facilitate RYK related tumours or sarcomas.

Another aspect of the present invention contemplates an assay for identifying or otherwise diagnosing abnormalities in RYK or for identifying or otherwise screening for a normal RYK molecule in a human. In accordance with this aspect of the invention, a source of genetic material is isolated from a human subject to be tested and subjected to Southern blot analysis, Northern blot analysis, Western blot analysis, radioimmunoassay (RIA) and other immunological techniques or variations or combinations of such analyses.

In one embodiment, there is provided a method for detecting an abnormal genomic coding sequence for a protein having receptor-type PTK-like properties in a human subject said method comprising contacting a genetic sample from said human subject with one or more oligonucleotide primers specific for a part of the naturally occurring genomic sequence for said protein or for an abnormal coding sequence for said protein for a time and under conditions sufficient for said oligonucleotide to hybridise to said genomic sequence and then screening for said hybridization.

In a more particular embodiment, a human subject is screened for a normal or abnormal RYK gene by isolating a genetic sample including genomic DNA from said human subject, subjecting said genetic sample to restriction endonuclease digestion to produce digested or partially digested DNA, subjecting said digested DNA to electrophoresis to separate the digested DNA based on length of fragments in the DNA digestion and screening the separated DNA digest to Southern blot analysis to screen for the presence or absence of particular regions of the RYK gene. For example, an oligonucleotide probe can be generated capable of screening for a nucleotide sequence corresponding to a "normal" extracellular region of RYK such as one or both of the leucine rich regions. In an abnormal RYK, the restriction pattern of this region may alter or contain deleted or duplicated sequences. Such an assay will screen for these modifications.

An "abnormal RYK" is defined inter alia at the genetic level as an alteration in the nucleotide sequence encoding normal RYK such as to result in a RYK molecule with an altered amino acid sequence such as an insertion, deletion and/or substitution. The altered RYK may also have a different glycosylation pattern relative to the naturally occurring (i.e. normal) RYK molecule. Such a change in glycosylation patterns can result from a change in a single amino acid residue. An "abnormal RYK" can be defined inter alia at the functional level as a molecule having altered ligand binding characteristics. Frequently, this can result in a tumour or sarcoma or a predisposition thereto.

The human subject may be an adult, adolescent, child, infant or a foetus.

The assay may be particularly useful in screening members of a family with a pre-disposition to cancer based on a defective or modified RYK molecule.

Yet another aspect of the present invention provides a fragment of mammalian RYK, said fragment containing a proteolytic cleavage site. The amino acid sequence constituting this site consists of Lys-Arg-Arg-Lys and such a cleavage site would be useful in engineered proteins, polypeptides or peptides to render these capable of enzymatic modification. For example, a diagnostic agent could be prepared comprising a reporter molecule connected to otherwise fused to a protein, polypeptide or peptide via the above-mentioned proteolytic cleavage site. The reporter molecule can then be cleaved off as part of the diagnostic assay.

The proteolytic cleavage site may also be useful in generating, truncated or cleaved molecules and/or fusion molecules.

The following single and three letter abbreviations for amino acid residues are used in the specification:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

EXAMPLE 1

MATERIALS AND METHODS

The following materials and methods are used in subsequent examples.

Cell Culture

Human cell lines were grown at 37° C. in a humidified atmosphere of 5% v/v $CO_2$ and maintained in RPMI-1640 medium plus the following supplements: 10% v/v foetal bovine serum, 10 mM glutamine, 100 units/ml penicillin and 12.5 µg/ml streptomycin (Commonwealth Serum Laboratories, Melbourne, Australia). The following human cell lines were used in this study: MCF-7 (adenocarcinoma of the breast; 9), CCRF-HSB-2 (T lymphoblastoid; 10).

Screening of cDNA libraries cDNA libraries were screened according to the methods elsewhere described (11). Clones of human RYK were isolated from an oligo dT primed Interleukin-1 stimulated human hepatoma cDNA library in lambda ZAP (Stratagene, La Jolla, Calif., cat#935202) using a 90 bp PCR fragment derived from the extracellular region of the mouse RYK cDNA sequence as a probe (12). To facilitate sequencing, the human clones described herein (pBS-XYZ and pBS-E; see FIG. 2) were subcloned into the EcoRV site of pBluescript II (Stratagene) using EcoRV linkers. cDNA libraries used were from murine NFS TPA activated spleen (Clontech cat.#ML1018), murine Swiss-albina 3T3 fibroblast (Clontech cat.#1023b) and murine ICR linoleic acid activated pleural macrophage (Clontech cat.#ML1005b) generated in λgt11. cDNA libraries from murine BALB/c testis (Clontech cat.#ML1020b) and murine day 10 embryonic neuro-epithelium (27) were generated in λgt10. Around $10^6$ recombinants of each of these libraries were screened on each occasion.

DNA Sequencing

A range of RYK specific oligonucleotide primers were used to sequence the RYK cDNA clones in addition to the universal primers of M13 (forward and reverse). To sequence the GC-rich 5' region, a number of smaller (150–300 base pair) fragments were generated and subcloned into the plasmid Bluescript II. DNA was sequenced by the dideoxynucleotide chain termination method (13). Sequence data were derived from complete analysis of both strands of the DNA.

Northern blotting

A 2.6 kb Pst I fragment from the Bluescript-XYZ clone was subcloned into the PstI site of Bluescript in order to transcribe an antisense RNA probe. This fragment represents the complete insert without the GC-rich 5' region, but includes the 3' untranslated region. In vivo synthesis of the $^{32}$-DUTP (100 µCi) labelled 2.6 kb message was performed using T3 RNA polymerase and the Message Maker Kit (Bresatec, Adelaide, Australia), Poly A+mRNA samples were prepared as described elsewhere (14). Aliquots (0.5 µg) were electrophoresed on a 1% w/v agarose gel containing 2.2 M formaldehyde; 20 mM MOPS, pH 6.8;1 mM EDTA; 5 mM sodium acetate, and transferred to GeneScreen Plus (cat# NEF-976; DuPont, NEN, Boston, Mass.). Filters were prehybridised for 16 hours in 50% v/v formamide containing 3×SSC; 5×Denharts; 10 mM Hepes pH 7.0; 100 µg/ml poly C, 100 µg/ml denatured herring sperm DNA; 10 µg/ml *E. coli* DNA; 0.1% w/v SDS, then hybridised with the $^{32}$P-labelled human riboprobe in the same solution for 18 hours at 42° C. Filters were washed at a final stringency of 0.1×SSC/0.1% w/v SDS at 65° C., followed by treatment with a solution of 1 µg/ml RNase A (Boehringer Mannheim GmbH, Mannheim, Germany)/2×SSC at room temperature for 15 minutes before exposure to Kodak XAR-5 X-ray film (Eastman-Kodak Company, Rochester, N.Y.) with two intensifying screens. Prior to transfer, gels were observed under UV illumination to ensure equivalent amounts of RNA were loaded in each lane.

Immunoprecipitation of the RYK polypeptide

MCF-7 cells (5×$10^6$) were grown in methionine/cysteine free medium (Flow Laboratories) containing 1 mCi $^{35}$S-methionine/cysteine (Translabel, ICN) for 6 hours prior to harvesting with PBS /20 mM EDTA. Cells were lysed with 5 ml of lysis buffer (10 mM Tris-HCl pH 8.0, 1% w/v Tx-100, 150 mM NaCl, 0.05% NaN$_3$, 0.2 mM PMSF, 5 mM Na2VO$_3$, 10 µg/ml leupeptin, 0.2 TIU/ml aprotinin) and nuclei and debris removed by centrifugation for 15 min in a microfuge at 4° C. The lysate was then precleared with 500 µl of protein A-Sepharose beads and 250 µl of pre-immune sera for 16 hours at 4° C. The beads were removed by centrifugation at 40,000 rpm in a Beckman ultracentrifuge using a Ti 50 rotor. Equal amounts of lysates (1 ml) were then incubated with 5 µl of either preimmune rabbit sera or rabbit anti-Keyhole Limpet Heamocyanin (KLH)-RYK peptide for 2 hours at 4° C. followed by the addition of 10 µl of protein-A-sepharose beads for a further 45 mins. Lysates were washed three times with lysis buffer followed by three washes with 10 mM Tris-HCl pH 8.0,150 mM NaCl, 0.1% v/v Tx-100. Immunoprecipitates were then eluted with 20 µl of SDS sample buffer in the presence or absence of 2% β-mercaptoethanol as the reducing agent. SDS-PAGE was performed according to the methods of Laemmli (15). After drying, the gels were autoradiographed using X-ray film (KODAK XAR-5) or using a Phosphorimage analyser and Imagequant v3.0 software (Molecular Dynamics, Sunnyvale, Calif.). Relative molecular weight markers were 200,000 (Myosin), 97,400 (Phosphorylase b), 69,000 (Bovine Serum Albumin), 46,000 (Ovalbumin), 30,000 (Carbonic anhydrase), 21,500 (Trypsin Inhibitor) and 14,300 (Lysozyme) (Rainbow markers, Amersham).

In vitro transcription/translation

In vitro translation of cDNA clones was performed using the TNT Coupled Reticulocyte Lysate System (Promega, Madison, Wis.). Human and mouse RYK cDNAs were subcloned into the expression vector pCDM8 using Bst XI linkers (Invitrogen; pCD.H.RYK and pCD.M.RYK). pCD.M.RYK, pCD.H.RYK, pCDM8 or control cDNAs (1 µg) were used as templates for the in vitr synthesis of protein products using T7 RNA Polymerase in the presence of $^{35}$S-methionine (1097 Ci/mmol, Translation grade, Amersham). Proteins were then treated with reducing SDS-PAGE sample buffer and analysed by SDS-PAGE.

Chromosomal localization

Lymphocyte cultures from two apparently normal males were used to prepare chromosomes using standard methods. Synchronization of cultures and G-banding were performed by the method of Zabel et al (16). A 1.6 kb fragment containing 3' untranslated regions of the RYK cDNA clone containing the intracellular domain and 550 bp of 3' untranslated region was labelled to a specific activity of 7.45×$10^7$ cpm/µg with [$^3$H]dATP, [$^3$H]dCTP and [$^3$H]dGTP and used to probe the chromosomal preparations. Hybridization to the chromosomes was performed at a concentration of 10.05–0.1 µg of probe per ml of fluid. The slides were developed using a 2:1 dilution of KODAK NTB-2 nuclear research emulsion with water after a period of 13 days. All individual silver grains that touched any chromosome within each metaphase were plotted on an ideogram (see FIG. 7).

Glutathione transferase fusion proteins

To demonstrate the kinase activity of the RYK molecule, fusion proteins between the cytoplasmic domain of RYK and glutathione transferase were constructed (FIG. 7A). This was achieved by ligating a PCR product representing the entire ryk cytoplasmic domain (from position 820 to the in frame stop of FIG. 2B) in frame to the sequence encoding glutathione-S-transferase in pGEX-3X (between the BamH1 and EcoR1 sites; (17) to produce the construct pGEX-CYT-RYK. The fusion protein was induced by addition of 0.1 mM IPTG to the culture two hours prior to harvesting as elsewhere described (17).

Protein kinase assays

The fusion protein of the RYK cytoplasmic domain and the gluthathione-S-transferase was extracted from the bacterial cells using 10 mM Tris-HC1 pH 7.5/5 mg/ml lysozyme/100 µM Na2VO$_4$ and solubilized with 1% Tx-100. Soluble proteins were immunoprecipitated with glutathione-Seharose beads. Immunoprecipitates were then placed in kinase buffer (10 mM Tris-HCl pH 7.5, 10 mM MgCl$_2$, 10 mM MnCl$_2$). Each immunoprecipitate (approx 10 µl of packed beads) was then incubated with xCi of carrier-free gamma-$^{32}$P-ATP (Amersham cat#101691) for 10 minutes at room temperature. After incubation, the excess label was removed by aspiration with a 30 gauge needle and the beads resuspended in SDS sample buffer, boiled and loaded onto an 8% w/v polyacrylamide gel for electrophoresis. SDS-PAGE was performed by the methods of Laemmli (15). After drying the gels were autoradiographed using X-ray film (KODAK XAR-5). Relative molecular weight markers were 200,000, 97,000, 67,000, 45,000, 30,000 and 20,000 (Amersham, Rainbow markers).

Computer-Aided Sequence Analysis

Comparisons of the amino acid sequences of mouse and human RYK were performed using an alignment programme from the Staden group of programmes on a VAX VMS 5.2. Phylogenetic analysis of the RYK protein/kinase domain (Leucine 329-Arginine 588) were performed using the procedure of Feng and Doolittle (18), based on the tree building concept of Fitch and Margoliash (19), using a micro VAXII-vms computer system.

EXAMPLE 2

ISOLATION AND SEQUENCE OF THE MOUSE RYK cDNA

Thirteen mouse cDNA libraries were screened in order to isolate a full-length cDNA clone. Two RYK mRNAs were identified and were 3.5 kb and 2.5 kb, respectively. One clone XZ represented an almost full-length copy of the 2.8 kb mRNA. The sequence of the RYK mRNA is presented in FIG. 4. The 5' end of this clone was extremely GC rich (88% in the region 5' of the putative initiation codon), a feature which perhaps explains the relative rarity of clones bearing this region of the RYK mRNA in any of the libraries screened.

There are two potential initiation methionine codons at the 5' end of the XZ clone (located at position 1 and −27 in FIG. 4). The ATG at position 1 is considered the most likely candidate for the start codon of RYK based on the following observations: i. there is a better candidate leader peptide following this methionine; ii. it is positioned immediately after the highly GC rich region of the XZ clone, (and not buried within it, as is the case for the methionine at position −27); iii. comparison of the mouse and human RYK coding sequences (see Example 3) shows a degeneration of the otherwise extremely high degree of homology between these two sequences immediately prior to this methionine. Initiation at position 1 would lead to an open reading frame of 1698 bases. The prediced RYK protein is therefore 566 amino acids long, with a predicted molecular mass of 63,598. daltons.

The predicted RYK protein bears all the features usually associated with membership of the growth factor receptor family of PTKs. Accordingly, the kinase domain is located towards the C-terminus of the protein (between the putative ATP binding site, -Gln-Glu-Gly-Ser-Phe-Gly- [located at amino acid position 295] and the most C-terminal conserved element [motif XI, (-CysTrp . . . ArgPro . . . Leu-) beginning at amino acid position 537 in FIG. 3].

The mouse RYK gene is expressed widely as two mRNAs of 2.8 kb and 3.5 kb in both mouse tissue mRNAs and in vitro cell lines. Highest levels of RYK are found in ovary, lung and placenta poly-(A+) RNA, although all of the tissues examined express detectable RYK mRNA. It is noteworthy that RYK mRNA is also expressed in the human mammary carcinoma cell line A431, but that only the larger mRNA species appears to be present.

EXAMPLE 3

CLONING AND SEQUENCING OF HUMAN RYK

A 90 bp PCR fragment corresponding to the 5' end of the mouse RYK cDNA clone was generated and used as a probe to isolate a number of clones from a human hepatoma cDNA library which were subsequently subcloned into the vector pBluescript for sequencing (see above). The clone pBS-XYZ(3.0 kb) was full length whilst pBS-E (2.7 kb) was missing sequence at the 5' end.

Northern blotting analysis

Figure 1B:
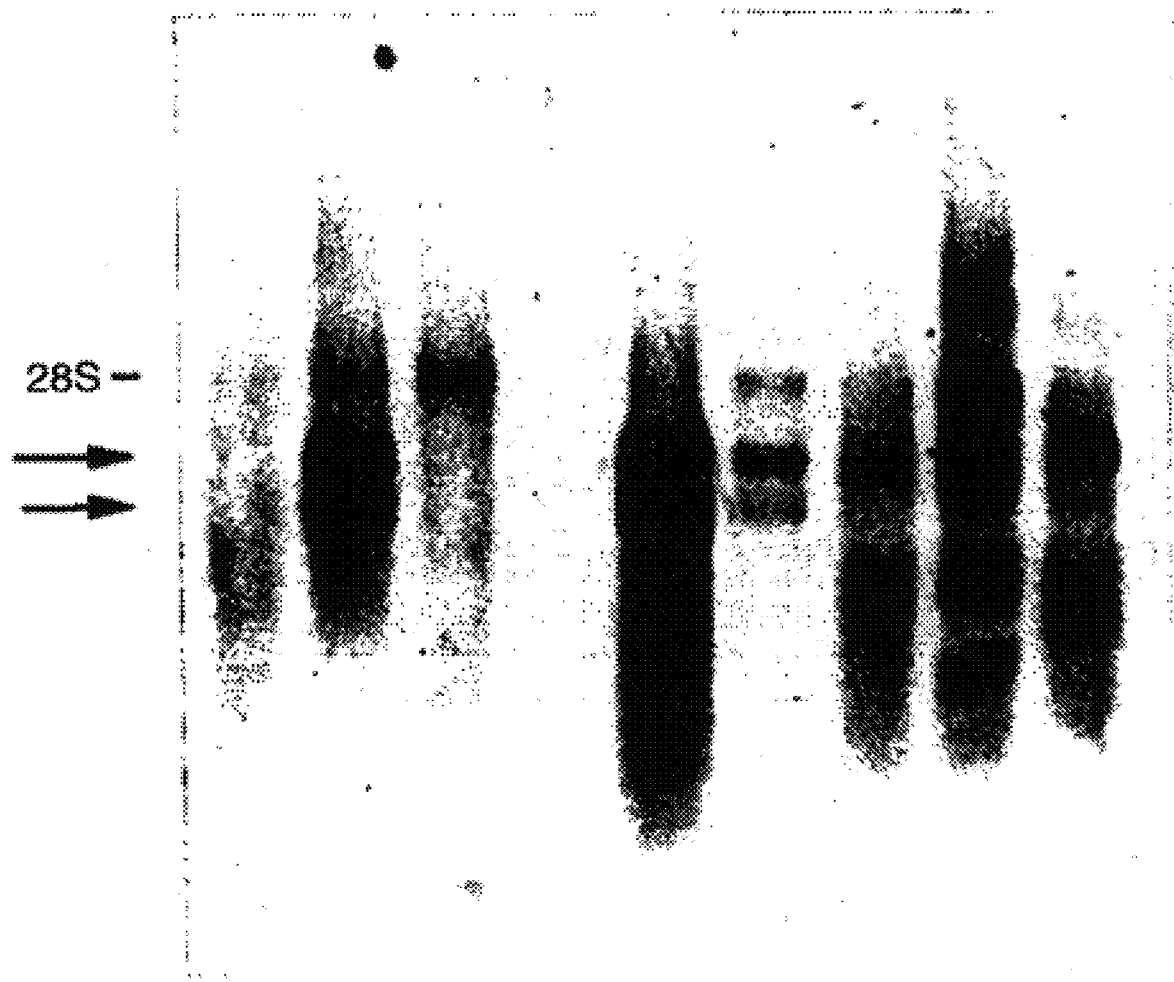
Figure 1C:
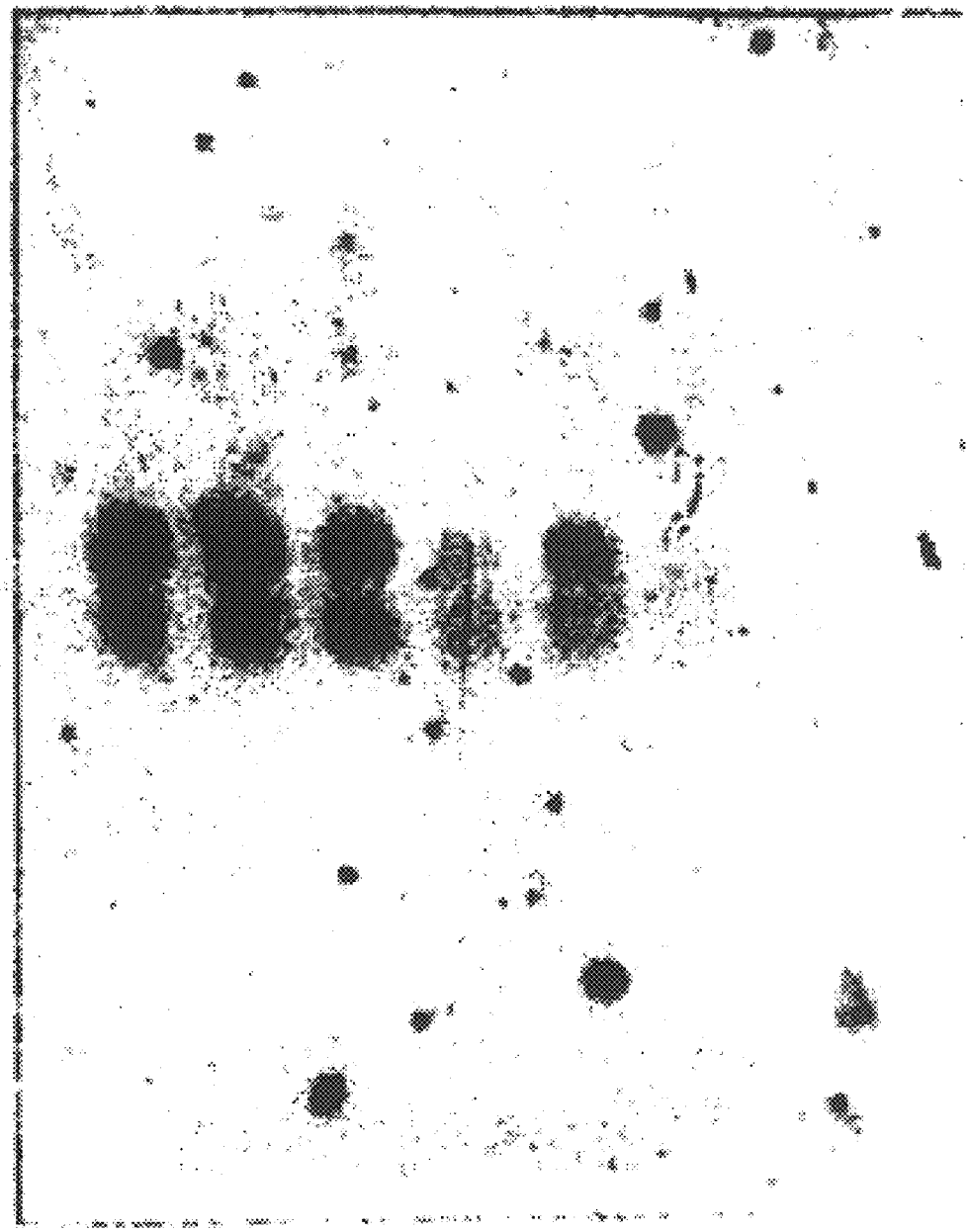

RYK mRNA appears to be broadly distributed on a range of normal tissues and in vito cell lines (FIG. 1A, B and C). Two species are detected in the mouse of 3.5 and 2.8 kb whereas in the human only the larger of the two species is present (lane 1, A431, FIG. 1). The two mRNA transcripts found in the mouse are likely to have been derived from the use of different polyadenylation signals. A tissue Northern demonstrated high levels of expression on the placenta, ovaries and lung while the 13 day embryo, kidneys and brain expressed significant amounts. Thymus and spleen expressed low levels indicating a tendency not to be expressed on cells of haematopoietic origin. FIGS. 1B and C show a wide distribution of RYK expression on in vitro cell lines including NIH-3T3, embryonic stem cell and the FDCP-1 cell line.

Organisation of the RYK gene product

The complete cDNA sequence of human RYK is contained within a 3067 bp clone (see FIG. 2B) isolated from an Interleukin-1 stimulated human hepatoma cDNA library. An open reading frame extends from nucleotide 54 for approximately 1.9 kb to an in frame stop codon (TGA) at position 1950. The methionine codon located at position 132–134 is designated herein as the translation initiation codon as it is preceded by an inframe stop codon at position 51 of the clone and followed by a hydrophobic stretch of amino acids typical of a leader sequence. In addition, the predicted size of human RYK translated from this start site corresponds with the size of the protein generated by in vito transcription/translation of pCD.H.RYK (see FIG. 9B). It should be noted that a leucine (CTG) at position 252–254 (amino acid position 41) could also potentially be a site for translation initiation. The sequence surrounding $CTG_{41}$ is consistent with the CC(A/G)CCATGG consensus sequence defined for mammalian initiation codons described by Kozak (20). By comparison, the sequence surrounding the ATG at position 1 differs from the "Kozak" consensus at the critical +4 and −3 positions. Although ATG is the most commonly used translation initiation codon, initiation of translation from CTG have been reported for a number of molecules including the tyrosine kinase hck (19).

It is noteworthy that a highly GC-rich region (nucleotides 19–250; 70–90% G+C content) characteristic of 5' untranslated regions of other receptor-type tyrosine kinases (growth factor receptors), transcription factors, DNA-binding proteins and proto-oncogenes (20) was found in the human RYK sequence. These regions are thought to be involved in the regulation of protein translation (20). Therefore, given that RYK is related to the family of growth factor receptors (see below) the poor "Kozak" sequence and the highly GC-rich 5' region may represent two potential mechanisms for translational control. The 3' untranslated region extends from the inframe stop codon over 1.1 kb to the poly A tail. A consensus signal sequence for polyadenylation (ATTAAA) lies just prior to this at position 3036–3041.

Domain structure of RYK

The amino acid sequence deduced from the human RYK cDNA contains all the key features of a typical transmembrane receptor (FIG. 2); that of a signal peptide, extracellular, transmembrane and cytoplasmic domains. Unprocessed RYK is a protein of 606 amino acids with a predicted molecular weight of 67,659 Daltons; slightly larger than the predicted size for mouse RYK (63,598 Daltons). Hydropathy analysis of the deduced sequence by the methods of Kyte and Doolittle (21) show a 28 amino acid hydrophobic domain which subdivides the molecule (FIG. 2). The C-terminal side of this sequence is bordered by a stretch of basic residues (Lys-Arg) typical of stop transfer sequences. This sequence, therefore, most likely represents a transmembrane domain. The cytoplasmic domain contains a large juxtamembrane region (84 amino acids) containing many serine residues. The extracellular domain of RYK contains 224 amino acids, which by comparison to other RTK members is relatively small. Contained within this domain are five potential N-linked glycosylation sites (Asn-X-Ser/Thr); their presence is further evidence that this region of the cDNA encodes for an extracellular domain. Based on the predictions of von Heijne (12), the cleavage site for the signal peptidase is N-terminal to $Ala_{25}$ producing a mature protein of some 582 amino acids. Comparison of the putative human RYK extracellular domain with extracellular domains of other known RTKs demonstrated no significant homology that would allow it to be placed into one of the six structurally related clusters of RTKs (23; 24). Two leucine-rich repeats are present in the extracellular domain of the human sequence (FIG. 2B). The leucine-rich regions are:

Leu-Ile-Glr-Leu-Asp-Ala-Glu-Leu-Tyr-Val-Arg-Asn-Asp-Leu-Ile-Ser-His-Tyr-Ala-Leu-Ser-Phe (SEQ. ID. NO.4);

and/or

Leu-Met-Gln-Leu-Asn-Leu-Thr-Val-Asn-Ser-Ser-Lys-Asn-Phe-Thr-Val-Leu-Asn-Phe-Lys-Arg-Arg-Lys (SEQ. ID. NO. 5).

RYK, therefore, possesses an extracellular domain which is unique in structure compared to other RTKs.

Human RYK kinase-like domain

The cytoplasmic portion of human RYK extends for 354 amino acids and contains all of the conserved motifs found in the protein tyrosine kinase family (FIG. 2; subdomains I–XI, 25). This begins with the putative ATP-binding site (Gln-Glu-Gly-Thr-Phe-Gly) located at amino acids 334–339 and ends with motif XI (-Cys-Trp . . . Arg-Pro . . . Leu) at position 577–591. There are alterations to several of the most highly conserved motifs held in common by members of the PTK and RTK families. In subdomain I of PTKs, the Rossman motif (32), thought to be associated with ATP binding, has three invariant glycine residues in a six amino acid cluster (Gly-X-Gly-X-X-Gly); human RYK has the sequence SEQ. ID. NO. 13 Gln-Glu-Gly-Thr-Phe-Gly which is similar to mouse RYK and unique within the kinase family. The Ala-X-Lys sequence characteristic of subdomain II cannot be found but two sequences Phe-X-Lys and Thr-X-Lys are both present close to the correct location Subdomains III to V of human RYK all contain the conserved motifs of the tyrosine kinase family as previously defined. Subdomain VIb of human RYK contains the conservative amino acid substitution of a lysine for a arginine in the motif SEQ. ID. NO: 4 (-His-Arg-Asp-Leu-Ala-Ala-Arg-Asn-; subdomain Vlb). Although conservative this is, however, a highly unusual change to a motif which is one of the most conserved in the PTK/RTK family. It is especially unusual given that the mouse sequence also has the conserved arginine residue. This lysine for arginine substitution was found in two independently derived clones (pBS-XYZ and pBS-E) so it is unlikely to represent a sequencing artefact. Further, the highly conserved Asp-Phe-Gly sequence of subdomain VII is altered to Asp-Asn-Ala in human RYK and is identical to the change to this redon in the mouse sequence (12). This is the most highly conserved motif within the protein kinase family. The only published exception to this is klg containing the sequence -Ala-Leu-Ser- (26).

In RYK, the -Gly-X-Gly-X-X-Gly- (SEQ. ID. NO. 1) motif has a glutamine at the first position. These changes to the catalytic domain of human RYK may reflect a unique nucleotide and/or substrate specificity for RYK. It is also possible that the substitutions are compensate for each other and thus allow kinase function to proceed as with mouse RYK.

The remaining subdomains (VIII–XI) of human RYK follow the conserved motifs of the tyrosine kinase family. It is noteworthy that the RYK sequence also contains residues characteristic of receptor-type tyrosine kinases such as the methionine in the sequence SEQ. ID. NO. 15 Arg-Trp-Met-Ala-Leu-Glu-Ser found in subdomain VII. Furthermore, between subdomains VII and VIII of human RYK is a tyrosine residue which is frequently used as an autophosphorylation site in the tyrosine kinase family, the sequence is -Met-Asp-Tyr-His (SEQ. ID. NO. 6) and is identical to mouse RYK.

Comparison of mouse and human RYK

Comparison of human and mouse RYK cDNA sequences demonstrates a high degree of conservation over almost their entire length with homology of 92% and 97% at the nucleotide and amino acid levels, respectively (FIG. 4). Both open reading frames terminate at the identical portion of their deduced amino acid sequence; after the sequence SEQ. ID. NO. 46 -His-Ala-Ala-Leu-Gly-Ala-Thr-Val-*. The most pronounced difference, however, is at the 5' end of the cDNA where the two sequences diverge from each other. After amino acid 55 of the human sequence, mouse and human amino acid sequences are greater than 95% identical; the sequences are only 15% identical prior to this point. Prior to amino acid 55, the human and mouse nucleotide sequences also become less similar even though both sequences remain high in GC content with some smaller areas of homology. The kinase domains of human and mouse RYK are more related to each other than any kinase domain found in the database (95% compared to 35–53% for other kinases). The human and mouse RYK sequences have unexpected differences at key regions within the conserved PTK motifs, for example the highly conserved arginine residue in the subdomain VIb is a lysine in the human sequence. Comparison of the kinase domains (FIG. 4) show only twelve amino acid changes in the PTK subdomains (I–XI) with the majority being conservative substitutions. The other amino acid changes between the mouse and human sequences are also, in general highly conservative substitutions. In addition to conservative substitutions, there is also a deletion of sequences between mouse and human RYK The human sequence has a deletion of three amino acids [-Ser-Ser-Gly-] in the region between the transmembrane domain and the putative ATP binding site compared to the mouse sequence. Furthermore, the human sequence contains an additional asparagine residue in subdomain IX not found in the deduced mouse sequence. In the human, this region is SEQ. ID. NO. 17 [-Val-Asn-Ser-Leu-Trp-Glu-Leu-Met-] and in the mouse SEQ. ID. NO. 18 [-Val-Thr-Leu-Trp-Glu-Leu-Met-]. All of these changes were found in both clones pBS-XYZ and pBS-E and therefore unlikely to be sequencing errors. The additional asparagine residue is highly unusual given the conserved spacing of residues seen in this motif (25).

RYK mRNA Expression in Human Cell Lines

In the mouse, RYK mRNA appears to be broadly distributed on a range of normal tissues and in vitro cell lines (Example 2). Northern blotting demonstrates the expression of a single species of mRNA found in the MCF-7 cell line; CCRF-HSB-2 showed no expression of RYK. Interestingly, two mRNA species (3.5 and 2.7 kb) are detected in the mouse whereas in the human only the larger message is present (FIG. 8). These differences are presumably due to use of alternative polyadenylation sites. Using the polymerase chain reaction, it was demonstrated that RYK is expressed in the epithelial cell line LIM-1863 of Whitehead et al (28) which is derived from normal colonic crypts.

Analysis of the human RYK polypeptide

In order to determine the size of the mature RYK protein, SDS-PAGE analysis of RYK was performed. Immunoprecipitation was performed from $^{35}$S-methionine labelled lysates of the human, adenocarcinoma of the breast cell line MCF-7 which by Northern blotting was shown to express RYK mRNA (FIG. 8). The antisera used was raised against a C-terminal peptide of mouse RYK SEQ. ID. NO: 19 (Lys-Phe-Gln-Gln-Leu-Val-Gln-Cys-Leu-Thr-Glu-Phe-His-Ala-Ala-Leu-Gly-Ala-Tyr-Val) which is highly conserved (95%) in the human RYK sequence. Using this antisera a species of Mr=85,000–90,000 was detected under both reducing and non-reducing conditions (FIG. 10A; I, reduced & non-reduced). This species was not precipitated using a pre-immune rabbit sera (FIG. 9A; PI, reduced & non-reduced). This result is consistent with the size of the polypeptide predicted from the human RYK cDNA given use of the five potential N-linked glycosylation sites. It is also consistent with the size of mouse RYK immunoprecipitated from NIH-3T3 cells. Under both reducing and non-reducing conditions, a band of Mr=35,000 was seen, which appeared specifically in the immunoprecipitates using the RYK antisera Its association with RYK is unclear. Non-reducing conditions produced a smear of >200,000 in addition to the 85,000–90,000 Mr species which could potentially represent aggregated receptor.

Figure 9B:
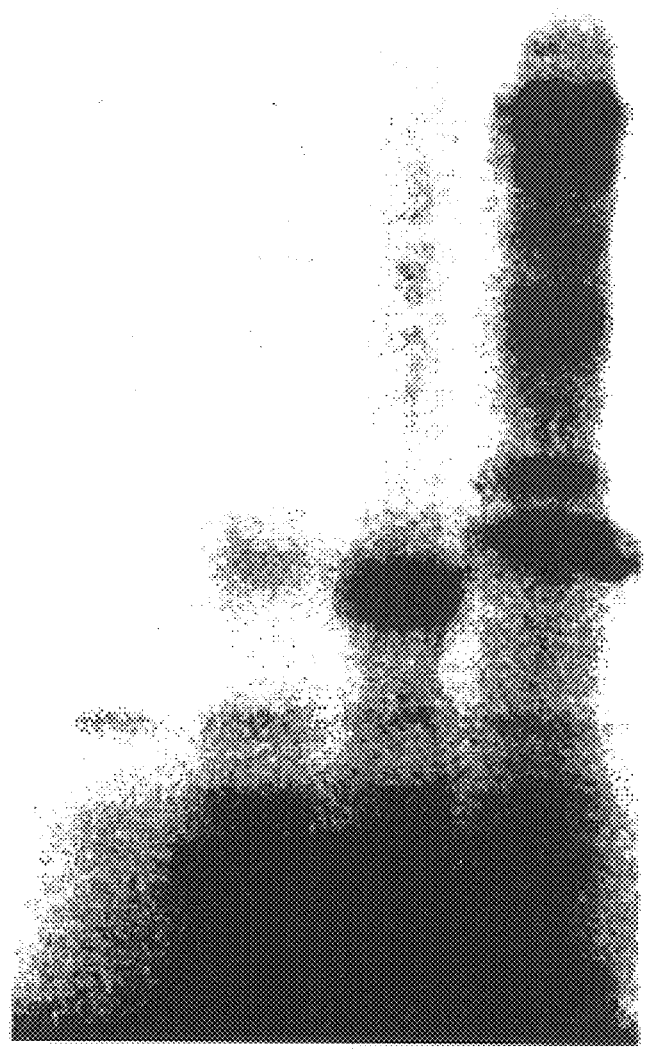

In vitro transcription/translation of the human RYK cDNA using 77 RNA Polymerase has demonstrated a protein product of around 65,000–70,000 by SDS-PAGE (FIG. 9B, pCD.H RYK). This is similar to the size of human RYK predicted from the human cDNA sequence. In comparison, the mouse cDNA gave a slightly smaller protein product (FIG. 9B, pCD.M.RYK) which is consistent with the human clone having a more 5' translational start site than the mouse. Further evidence to support this comes from the comparison of RYK immunoprecipitated from MCF-7 (human) and NIH-3T3 (mouse) which shows that human RYK is marginally larger by about 2–4 kd. The quantitative ratio of products produced by both plasmids in the in vitro transcription/translation assay was also different and could be due to the higher GC-rich content of the human RYK 5' end. The protein product of both the mouse and human RYK cDNA clones also contained two identical smaller species of Mr=40,000–45,000 which are RYK specific, possibly due to false translational start sites. Control DNA produced no specific bands whereas the positive control plasmid pCD-NYK yielded a 170,000 species plus a number of smaller species; none of which correlated with the species seen with the RYK cDNAs (FIG. 9B). The immunoprecipitation studies correlate well with the cDNA cloning and suggest that the human RYK cDNA encodes the sequence of the entire RYK polypeptide.

Chromosomal Mapping of RYK

The in situ staining of chromosomes from normal male lymphocytes show that of 160 silver grains on 38 metaphases, 22 (13.75% of all grains) were on chromosome 3 in the region 3q13.3 to 3q25, and 24 (15% of all grains) were on the short arm of chromosome 17 (see FIG. 7). Similar results were obtained from hybridization of the probe to the chromosomes of the second normal male. A second series of experiments demonstrated a preference for staining of chromosome 3 with less pronounced staining on chromosome 17. These results indicate that the gene encoding RYK is found on chromosome 3 in the human.

EXAMPLE 4

TRUNCATED AND FUSION RYK MOLECULES: METHODS

A series of mutants, truncated forms and fusion hybrids of human and mouse RYK are obtainable using oligonucleotide directed mutagenesis. The RYK cDNA clones were subcloned into the expression vector pCDM8 (30) and single stranded (ss) ULP+DNA of RYK was made. This ssUTP+ DNA is then used as a template for annealing a mutagenic oligonucleotide which encodes a region or part of RYK together with the change or changes to be introduced to that region or part. A second strand of DNA is then generated by transformation into the appropriate strain of bacteria which provides a selection against the wild type strand. Mutations are then selected by preparing DNA from these bacteria and analysing same by restriction enzyme digestion or nucleotide sequencing.

Alternatively, using standard restriction digestion and ligation procedures, a series of hybrid cDNA molecules are prepared carrying, for example, the 5' end of human RYK cDNA and the 3' end of murine RYK cDNA or the 3' end of murine RYK cDNA or the 3' end of growth factor receptor cDNA (e.g. EGFR). A vast array of hybrid or fusion molecules are obtainable by such a procedure.

EXAMPLE 5

TRUNCATED AND FUSION RYK MOLECULES—I

The extracellular portion of RYK was fused to the kinase domain of the EGF receptor. A mutant form of mouse RYK cDNA was produced which contained a KpnI restriction site (GGTACC) within the transmembrane domain of RYK (glycine 190 and valine 191). A KpnI site was also introduced into the transmembrane domain of the human EGF receptor at glycine 628 and alanine 629. Utilizing the KpnI site located in the expression vector pCDM8 the kinase domains of the two receptors were switched.

EXAMPLE 6

TRUNCATED AND FUSION RYK MOLECULES—II

The extracellular portion of the EGFR was fused to the kinase domain of RYK as described in Example 5.

EXAMPLE 7

TRUNCATED AND FUSION RYK MOLECULES—III

Secreted forms of mouse and human RYK extracellular domains were produced. An inframe stop codon was introduced at valine 184 in the mouse sequence and valine 225 in the human sequence. This valine residue lies at the N-terminal border of the transmembrane domain. These mutations were introduced by site-directed mutagenesis and selected through the addition of a diagnostic restriction site.

EXAMPLE 8

A TRUNCATED AND FUSION RYK MOLECULES—IV

A chimera between the RYK extracellular domain and the immunogenic peptide FLAG (IBI/Kodak) was made to allow purification of the presumed ligand binding domain of RYK using the FLAG biosystem (M2 antibody). To achieve this, a mutant of the RYK cDNA was made which contained an inframe BglII site at the junction between the extracellular domain and the transmembrane domain of RYK. The BglII site (AGATCT) was introduced in place of the sequence GTGTTT which encodes valine 184 and phenylalanine 185 in the mouse sequence. The sequence encoding the FLAG peptide is provided by synthetic oligonucleotide linkers which also contain preformed BglII sites on either end for ligation to the BglII site on the extracellular domain of RYK. The end result is the fusion of RYK extracellular domain inframe to the FLAG peptide.

EXAMPLE 9

TRUNCATED AND FUSION RYK MOLECULES—V

The mouse RYK kinase domain was ligated to the FLAG peptide in the pFLAG expression vector (IBI). The FLAG peptide is ligated inframe at the N-terminus of the kinase domain. The human RYK kinase domain was ligated to GST as a fusion protein in the vector pGEX (29). A BamHI (5')-EcoRI (3') PCR fragment representing the cytoplasmic domain of RYK from the C-terminal border of the transmembrane domain to the in frame stop codon of the mature sequence ligated into the BamHI/EcoRI sites of pGEX.

EXAMPLE 10

TRUNCATED AND FUSION RYK MOLECULES—VI

The RYK extracellular domain was fused in frame to secreted alkaline phosphatase, using the vector AP-tag-1 (31). A Hind III (5') -BglII (3') fragment of pCD-M-RYK-BglII was subcloned into Hind III-BglII digested AP-tag-1. This achieves the inframe ligation of the mouse RYK extracellular domain and secreted alkaline phosphatase.

EXAMPLE 11

IDENTIFICATION OF LIGANDS TO RYK MOLECULES

Two approaches were used to identify ligands for RYK. These involve: i) transfection of RYK into the factor-dependent cell line FDCP-1 (33) with subsequent rescue using a RYK-ligand; and ii) using a tagged version of the RYK extracellular domain (FLAG, AP, $^{125}$I) to screen an expression library.

Constructs for these expression studies were made using methods based on oligonucleotide directed mutagenesis to introduce unique restriction sites or termination codons and thus allow the precise subcloning of appropriate DNA fragments.

Initially, the full length clones of human RYK, mouse RYK and human EGFR were subcloned into the expression vector pCDM8 (30) to enable the generation of single stranded UTP+DNA for site-directed mutagenesis. In addition, this vector permits in vitro transcription/translation, transient expression in COS cells as well as co-transfection with pgKNEO for expression in FDCP-1 cells.

To produce secreted forms of RYK and the EGFR, termination codons were introduced at the predicted border of the extracellular and transmembrane domain of the receptors.

To study the function of RYK, transfected into FDCP-1 cells, a series of chimeric molecules between RYK and the EGFR were made. These constructs consist of the EGFR cytoplasmic domain ligated to the putative ligand-binding domain of RYK plus the converse, RYK cytoplasmic domain coupled to the EGFR extracellular region. These chimeras were made using a KpnI site which was introduced into the transmembrane domain of the three receptors by mutagenesis. Using a KpnI site already in the vector pCDM8 (position 3572) fragments of the receptors can be readily exchanged. The chimeras are useful for examining whether the RYK catalytic domain can transmit a mitogenic signal through stimulation of the EGFR extracellular domain with EGF. In addition, the RYK-EGFR chimera is usable in case the RYK cytoplasmic domain is unable to generate a mitogenic response.

Another approach involves the ligation of the extracellular domain of RYK to secreted alkaine phosphatase using the vector AP-TAG-1 (31). BglII sites were introduced into mouse and human RYK at the junction of extracellular domain and the transmembrane domain to allow inframe ligation to secreted alkaline phosphatase. These constructs have been produced and will be co-transfected with pBS-NEO into NIH-3T3 cells for production of a tagged affinity reagent.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Ullrich, A. and Schlessigner, J., (1990). Cell 61; 203–212.
2. Carpenter, G., & Cohen, S., (1990). J. Biol. Chem. 265, 7709–7712.
3. Wllliams, L. T., (1989). Science 243, 1564–1570.
4. Yeung, Y. G., Jubinsky, P. T., Sengupta, A., Yeung, D. C. Y., & Stanley, E. R., (1987). Proc. Natl. Acad. Sci. USA 84, 1268–1271.
5. Yarden, Y. and Ulrich, A., (1988). Ann. Rev. Biochem. 57: 443–478.

6. Bishop, J. M., (1983). Ann. Rev. Biochem 52: 301–354.
7. Hunter, T. and Cooper, J. A., (1985). Ann. Rev. Biochem 54: 987–930.
8. Resh, M., (1990). Oncogenes: 1437–1444.
9. Soule, H. D., Vazquez, J., Albert, A. L. S. & Brennan, R. (1973). J. Natl. Cancer Inst., 51, 1409–1416.
10. Adams, R., Flowers, A., & Davis, B. J. (1968). Cancer Res., 28, 1121–1125.
11. Sambrook, J., Fritsch, E. F., & Maniatis, T. (1989). Molecular Cloning A Laboratory Manual, 2nd Edition, Cold Spring Harbor Laboratory Press.
12. von Heijne, G. (1985) Nucl. Acids Res., 14, 4683–4690.
13. Sanger, F., Nicklen, S., & Coulson, A. R. (1977). Proc. Natl. Acad.Sci. (USA), 74, 5463–5467.
14. Wilks, A. F. & Kurban, R. R.(1988). Oncogene, 3, 289–294.
15. Laemmli, U. K. (1970). Nature (London), 227, 680–685.
16. Zabel, B. U., Naylor, S. L., Sakaguchi, A. Y., Bell, G. I, and Shows, T. B. *Proc. Natl. Acad. Sci. USA* 80; 6932–6936, 1983.
17. Smith, D. B. and Johnson. K. S., *Gene 67; 31–40, 1988*.
18. Feng, D. -F., & Doolittle, R. F. (1987). J.Mol.Evol., 25, 351–360.
19. Fitch, W. M., & Margoliash, E.(1967). Science, 12, 279–284.
20. Kozak, M. (1984). Nucl. Acids Res., 12, 857–872.
21. Kyte, J. & Doolittle, R. F.(1982). J.Mol.Biol, 157, 105–132.
22. Kozak, M. (1991). J. Cell Biol., 115, 887–903.
23. Yarden, Y. & Ullrich, A (1988). Ann. Rev. Biochem. 57, 443–478.
24. Wilks, A. F. (1992). Advances Canc. Res., 60,43–73.
25. Hanks, S. K., Quinn, A. M., & Hunter, T. (1988). Science, 241, 42–52.
26. Chou, Y. -H. & Hayman, M. J. (1991). Proc. Natl. Acad. Sci. (USA), 88,4897–4901.
27. Reid, H. H., Wilks, A. F. & Bernard, O. (1990). Proc. Natl. Acad. Sci. (USA), 87: 1596–1600.
28. Whitehead, R. H., Jones, J. K., Gabriel, A and Lukies, R. E. (1988) Cancer Res. 47: 2683–2689.
29. Smith, D. B. and Johnson, K. S. (1988) Gene 67: 31–40.
30. Aruffo, A. and Seed, B. (1987) Proc. Natl. Acad. Sci. USA 84: 8573.
31. Flanagan, J. T. and Leder, P. (1990) Cell 63: 185–194.
32. Knighton, D. R. et al (1991) Science: 253: 407–414.
33. Dexter, T. M. et al(1980) J. Exp. Med: 152: 1036–1047.

What is claimed is:

1. An isolated, protein tyrosine kinase receptor which has a molecular weight of from about 85 to about 90 kilodaltons as determined by SDS-PAGE, said receptor being further characterized by having an extracellular domain comprising:
   (i) two leucine rich regions, defined by SEQ ID NOS: 4 and 5, which are positioned in said receptor at a point N-terminal to
   (ii) an ATP binding site defined by the amino acid sequence set forth in SEQ ID NO: 2, which is positioned N-terminal to
   (iii) a kinase catalytic domain comprising amino acid sequence Asp-Asn-Ala.

2. The isolated receptor of claim 1, wherein the first Xaa in SEQ ID NO: 2 is Glu.

3. The isolated receptor of claim 1, wherein the second Xaa in SEQ ID NO: 2 is Ser or Thr.

4. The isolated receptor of claim 1, wherein the third Xaa in SEQ ID NO: 2 is Phe.

5. The isolated receptor of claim 1, wherein said ATP binding site is Gln-Glu-Gly-Thr-Phe-Gly (SEQ ID NO: 13).

6. The isolated receptor of claim 1, wherein said ATP binding site is Gln-Glu-Gly-Ser-Phe-Gly (SEQ ID NO: 6).

7. The isolated receptor of claim 1, having an amino acid sequence encoded by the nucleotide sequence of SEQ ID NO: 7.

8. The isolated receptor of claim 1 comprising an amino acid sequence selected from the group consisting of SEQ ID NO: 20 and SEQ ID NO: 9.

9. An isolated nucleic acid molecule which encodes the isolated protein tyrosine kinase receptor of claim 1.

10. The isolated nucleic acid molecule of claim 9, comprising a nucleotide sequence which encodes the protein encoded by the nucleotide sequence of SEQ ID NO: 7.

11. An isolated tyrosine kinase like protein receptor which has an amino acid sequence encoded by the nucleotide sequence of SEQ ID NO: 8.

12. An isolated nucleic acid molecule comprising the nucleotide sequence of SEQ ID NO: 8, wherein said isolated nucleotide acid molecule encodes a protein tyrosine kinase receptor.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
        (A) LENGTH:  6
        (B) TYPE:  amino acid
        (D) TOPOLOGY: linear (ii) MOLECULE TYPE: protein (xi) SEQUENCE DESCRIPTION:  SEQ ID NO: 1:

Gly Xaa Gly Xaa Xaa Gly
5

(2) INFORMATION FOR SEQ ID NO: 2:

(i) SEQUENCE CHARACTERISTICS:
        (A) LENGTH: 6
        (B) TYPE: amino acid
        (D) TOPOLOGY: linear (ii) MOLECULE TYPE: protein (xi) SEQUENCE DESCRIPTION: SEQ ID NO: 2:

Gln Xaa Gly Xaa Xaa Gly
            5

(2) INFORMATION FOR SEQ ID NO: 3:

(i) SEQUENCE CHARACTERISTICS:
        (A) LENGTH:  6

(B) TYPE: amino acid
          (D) TOPOLOGY: linear (ii) MOLECULE TYPE: protein (xi) SEQUENCE DESCRIPTION: SEQ ID NO: 3:

Gln Glu Gly Xaa Phe Gly
              5

(2) INFORMATION FOR SEQ ID NO: 4:

(i) SEQUENCE CHARACTERISTICS:
          (A) LENGTH: 23
          (B) TYPE: amino acid
          (D) TOPOLOGY: linear (ii) MOLECULE TYPE: protein (xi) SEQUENCE DESCRIPTION: SEQ ID NO: 4:

Leu Ile Gly Leu Asp Ala Glu Leu Tyr Tyr Val Arg Asn Asp Leu Ile
              5                  10                  15

Ser His Tyr Ala Leu Ser Phe
          20

(2) INFORMATION FOR SEQ ID NO: 5:

(i) SEQUENCE CHARACTERISTICS:
          (A) LENGTH: 23
          (B) TYPE: amino acid
          (D) TOPOLOGY: linear (ii) MOLECULE TYPE: protein (xi) SEQUENCE DESCRIPTION: SEQ ID NO: 5:

Leu Met Gln Leu Asn Leu Thr Val Asn Ser Ser Lys Asn Phe Thr Val
              5                  10                  15

Leu Asn Phe Lys Arg Arg Lys
          20

(2) INFORMATION FOR SEQ ID NO: 6:

(i) SEQUENCE CHARACTERISTICS:
          (A) LENGTH: 6
          (B) TYPE: amino acid
          (D) TOPOLOGY: linear (ii) MOLECULE TYPE: protein (xi) SEQUENCE DESCRIPTION: SEQ ID NO: 6:

Gln Glu Gly Ser Phe Gly
              5

(2) INFORMATION FOR SEQ ID NO: 7:

(i) SEQUENCE CHARACTERISTICS:
          (A) LENGTH: 3069
          (B) TYPE: nucleic acid
          (C) STRANDEDNESS: single
          (D) TOPOLOGY: linear (xi) SEQUENCE DESCRIPTION: SEQ ID NO: 7:

AACGGTATCG ATAAGCTTGA TATCGAATTC CGCACCCCCG GCTCGGGGCT GTGAGCGGCT      60

CGGGGCCGGG GGTGGGCGGC GGTGCGGCGG GCGGCCGACG CTCCTCTTCG GCGGCGGCGG     120

CGGCGGCGGC CC ATG CGT GGG GCG GCG CGG CTG GGG CGG CCG GGC CGG AGT    171
              Met Arg Gly Ala Ala Arg Leu Gly Arg Pro Gly Arg Ser
                   5                      10

```
TGC CTC CCG GGG CCC GCG CTG AGG GCC GCC GCC GCC CCC GCC CTG CTG          219
Cys Leu Pro Gly Pro Ala Leu Arg Ala Ala Ala Pro Ala Leu Leu
     15                  20                  25

CTT GCT CGT TGC GCT GTT GCC GCT GCT GCC GGC CTG CGT GCC GCC GCC          267
Leu Ala Arg Cys Ala Val Ala Ala Ala Ala Gly Leu Arg Ala Ala Ala
 30              35                  40                  45

CGT CCG CGG CCC CCG GAG CTG CAG TCG GCT TCC GCG GGG CCC AGC GTG          315
Arg Pro Arg Pro Pro Glu Leu Gln Ser Ala Ser Ala Gly Pro Ser Val
                 50                  55                  60

AGT CTC TAC CTG AGC GAG GAC GAG GTG CGC CGG CTG ATC GGT CTT GAT          363
Ser Leu Tyr Leu Ser Glu Asp Glu Val Arg Arg Leu Ile Gly Leu Asp
             65                  70                  75

GCA GAA CTT TAT TAT GTG AGA AAT GAC CTT ATT AGT CAC TAC GCT CTA          411
Ala Glu Leu Tyr Tyr Val Arg Asn Asp Leu Ile Ser His Tyr Ala Leu
 80                  85                  90

TCC TTT AAT CTG TTA GTA CCC AGT GAG ACA AAT TTC CTG CAC TTC ACC          459
Ser Phe Asn Leu Leu Val Pro Ser Glu Thr Asn Phe Leu His Phe Thr
     95                 100                 105

TGG CAT GCG AAG TCC AAG GTT GAA TAT AAG CTG GGA TTC CAA GTG GAC          507
Trp His Ala Lys Ser Lys Val Glu Tyr Lys Leu Gly Phe Gln Val Asp
110                 115                 120                 125

AAT GTT TTG GCA ATG GAT ATG CCC CAG GTC AAC ATT TCT GTT CAG GGG          555
Asn Val Leu Ala Met Asp Met Pro Gln Val Asn Ile Ser Val Gln Gly
                130                 135                 140

GAA GTT CCA CGC ACT TTA TCA GTG TTT CGG GTA GAG CTT TCC TGT ACT          603
Glu Val Pro Arg Thr Leu Ser Val Phe Arg Val Glu Leu Ser Cys Thr
            145                 150                 155

GGC AAA GTA GAT TCT GAA GTT ATG ATA CTA ATG CAG CTC AAC TTG ACA          651
Gly Lys Val Asp Ser Glu Val Met Ile Leu Met Gln Leu Asn Leu Thr
        160                 165                 170

GTA AAT TCT TCA AAA AAT TTT ACC GTC TTA AAT TTT AAA CGA AGG AAA          699
Val Asn Ser Ser Lys Asn Phe Thr Val Leu Asn Phe Lys Arg Arg Lys
        175                 180                 185

ATG TGC TAC AAA AAA CTT GAA GAA GTA AAA ACT TCA GCC TTG GAC AAA          747
Met Cys Tyr Lys Lys Leu Glu Glu Val Lys Thr Ser Ala Leu Asp Lys
190                 195                 200                 205

AAC ACT AGC AGA ACT ATT TAT GAT CCT GTA CAT GCA GCT CCA ACC ACT          795
Asn Thr Ser Arg Thr Ile Tyr Asp Pro Val His Ala Ala Pro Thr Thr
                210                 215                 220

TCT ACG CGT GTG TTT TAT ATT AGT GTA GGG GTT TGT TGT GCA GTA ATA          843
Ser Thr Arg Val Phe Tyr Ile Ser Val Gly Val Cys Cys Ala Val Ile
            225                 230                 235

TTT CTC GTA GCA ATA ATA TTA GCT GTT TTG CAC CTT CAT AAT ATG AAA          891
Phe Leu Val Ala Ile Ile Leu Ala Val Leu His Leu His Asn Met Lys
        240                 245                 250

AGG ATT GAA CTG GAT GAC AGC ATT AGT GCC AGC AGT AGT TCC CAA GGG          939
Arg Ile Glu Leu Asp Asp Ser Ile Ser Ala Ser Ser Ser Gln Gly
        255                 260                 265

CTG TCT CAG CCA TCC ACC CAG ACG ACT CAG TAT CTG AGA GCA GAC ACG          987
Leu Ser Gln Pro Ser Thr Gln Thr Thr Gln Tyr Leu Arg Ala Asp Thr
270                 275                 280                 285

CCC AAC AAT GCA ACT CCT ATC ACC AGT TAT CCT ACC TTG CGG ATA GAG         1035
Pro Asn Asn Ala Thr Pro Ile Thr Ser Tyr Pro Thr Leu Arg Ile Glu
                290                 295                 300

AAG AAC GAC TTG AGA AGT GTC ACT CTT TTG GAG GCC AAA GGC AAG GTG         1083
Lys Asn Asp Leu Arg Ser Val Thr Leu Leu Glu Ala Lys Gly Lys Val
            305                 310                 315

AAG GAT ATA GCA ATA TCC AGA GAG AGG ATA ACT CTA AAA GAT GTA CTC         1131
Lys Asp Ile Ala Ile Ser Arg Glu Arg Ile Thr Leu Lys Asp Val Leu
```

```
              320                 325                 330
CAA GAA GGT ACT TTT GGG CGT ATT TTC CAT GGG ATT TTA ATA GAT GAA          1179
Gln Glu Gly Thr Phe Gly Arg Ile Phe His Gly Ile Leu Ile Asp Glu
        335                 340                 345

AAA GAT CCA AAT AAA GAA AAA CAA GCA TTT GTC AAA ACA GTT AAA GAT          1227
Lys Asp Pro Asn Lys Glu Lys Gln Ala Phe Val Lys Thr Val Lys Asp
350                 355                 360                 365

CAA GCT TCT GAA ATT CAG GTG ACA ATG ATG CTC ACT GAA AGT TGT AAG          1275
Gln Ala Ser Glu Ile Gln Val Thr Met Met Leu Thr Glu Ser Cys Lys
                370                 375                 380

CTG CGA GGT CTT CAT CAC AGA AAT CTT CTT CCT ATT ACT CAT GTG TGT          1323
Leu Arg Gly Leu His His Arg Asn Leu Leu Pro Ile Thr His Val Cys
                385                 390                 495

ATA GAA GAA GGA GAA AAG CCC ATG GTG ATA TTG CCT TAC ATG AAT TGG          1371
Ile Glu Glu Gly Glu Lys Pro Met Val Ile Leu Pro Tyr Met Asn Trp
            400                 405                 410

GGG AAT CTT AAA TTG TTT TTA CGA CAG TGC AAG TTA GTA GAG GCC AAT          1419
Gly Asn Leu Lys Leu Phe Leu Arg Gln Cys Lys Leu Val Glu Ala Asn
        415                 420                 425

AAT CCA CAG GCA ATT TCT CAG CAA GAC CTG GTA CAC ATG GCT ATT CAG          1467
Asn Pro Gln Ala Ile Ser Gln Gln Asp Leu Val His Met Ala Ile Gln
430                 435                 440                 445

ATT GCC TGT GGA ATG AGC TAC CTG GCC AGA AGG GAA GTC ATC CAC AAA          1515
Ile Ala Cys Gly Met Ser Tyr Leu Ala Arg Arg Glu Val Ile His Lys
                450                 455                 460

GAC CTG GCT GCC AGG AAC TGT GTC ATT GAT GAC ACA CTT CAA GTT AAG          1563
Asp Leu Ala Ala Arg Asn Cys Val Ile Asp Asp Thr Leu Gln Val Lys
                465                 470                 475

ATC ACA GAC AAT GCC CTC TCC AGA GAC TTG TTC CCC ATG GAC TAT CAC          1611
Ile Thr Asp Asn Ala Leu Ser Arg Asp Leu Phe Pro Met Asp Tyr His
            480                 485                 490

TGT CTG GGG GAC AAT GAA AAC AGG CCA GTT CGT TGG ATG GCT CTT GAA          1659
Cys Leu Gly Asp Asn Glu Asn Arg Pro Val Arg Trp Met Ala Leu Glu
        495                 500                 505

AGT CTG GTT AAT AAC GAG TTC TCT AGC GCT AGT GAT GTG TGG GCC TTT          1707
Ser Leu Val Asn Asn Glu Phe Ser Ser Ala Ser Asp Val Trp Ala Phe
510                 515                 520                 525

GGA GTG AAC AGC TTG TGG GAA CTC ATG ACT CTG GGC CAG ACT CCC TAC          1755
Gly Val Asn Ser Leu Trp Glu Leu Met Thr Leu Gly Gln Thr Pro Tyr
                530                 535                 540

ACG TTG GAC ATT GAC CCC TTC GAG ATG GCG GCA TAC CTG AAA GAT GGT          1803
Thr Leu Asp Ile Asp Pro Phe Glu Met Ala Ala Tyr Leu Lys Asp Gly
                545                 550                 555

TAC CGA ATA GCC CAG CCA ATC ACC TGT CCT GAT GAA TTA TTT GCT GTG          1851
Tyr Arg Ile Ala Gln Pro Ile Thr Cys Pro Asp Glu Leu Phe Ala Val
            560                 565                 570

ATG GCC TGT TGC TGG GCC TTA GAT CCA GAG GAG AGG CCC AGG TTT CAG          1899
Met Ala Cys Cys Trp Ala Leu Asp Pro Glu Glu Arg Pro Arg Phe Gln
        575                 580                 585

CAG CTG GTA CAG TGC CTA ACA GAG TTT CAT GCA GCC CTG GGG GCC TAC          1947
Gln Leu Val Gln Cys Leu Thr Glu Phe His Ala Ala Leu Gly Ala Tyr
590                 595                 600                 605

GTC                                                                      1950
Val

TGACTCCTCT CCAATCCCAC ACCATCAGGA AGAAGGTGCC TGTCGGGGCT CACTTGAAGC        2010

CTGTCAGGGA TGCTTTGTAT ATCTAACACA ACGCCAACAG AAGCACATTT GTCTTCCAGA        2070

ACACCGTGCC TTAGAAATGC TTTAGAATCT GAACTTTTTA AGACAGACTT AATAATGTGG        2130
```

-continued

```
CATATTTTCT AGATATCACT TTTATTAGGT TGAACTGAAA GGGTTTTTGT AAATTTTTTG      2190

GCCAAAATTT TTTAAAACAT ACTTACTTTG GACTAGGGGT ACATTCTTAC AAAATAAATA      2250

AACAGTTTTT AAAATTGTTT AGACACAGAT ATTTGGAATT AGCTATCTTA GTGCCAACTG      2310

CTTTTTATTT TTTTACTTCA TCAAGGTGAT GTAAGTGACT TTGTTTAGAC ACAGATATTT      2370

GGAATTAGCC TATCTTAGTG CCAACTGCTT TTTATTTTTT TCCTTCATCA AGGTGATGTA      2430

AGTGACTCAC CTTTAAAGTT TTTTTAGTGT TATTTTTTAT CACTACTCTG GGAAATGGTT      2490

TGTCTTCAAG ATGCAATACT TTTCTTAGTA AAGGAAAAAC AGCATAAAAA GATACCTGGT      2550

CTGCCTTGTA CAAGAAAACC GAATATTAGA GGAAGAAAAT TTAAAGAAAA GCTAGAGAAA      2610

AAAAAAATTT TTTAAAAAAT ACTTATTAGA AGCAAACTGC CCTTGCATGG AAAACTGTTT      2670

ATTTTTTTCA GTGAAAAAGG AATTCTGCTT TCGTGTTTTT GGGAAAGCAG GAACTGAGTT      2730

CATTACATCT TTAATTTGGC AGAAATTAGC CTTTCTGTGA ACCAGATGTG GTTTGGGGCA      2790

GATCTGTAGT AAACAATGGT GATTTTATTT ATTTTTACTC TCTGGAAAAG GAGATAATAC      2850

AATTCCAGAA AGTGAACTCA TATTTCTAAG GTAAGATCCC TTTTATGCAC CTAGAATATG      2910

CTATGCACAG AGCGGGTGCT TGAGTTGTTG TCGTTTTTTG TTTGTTTTTT AAATGTAAAC      2970

TGGTAAATTT TGTGCTTATC TTCAAGGCTG GCTTAAGTAT AAAATTGTTT TTTAAACACT      3030

TGAAAAATTA AAGGATTTGT TTTATATTAA AAAAAAAA                              3069

(2) INFORMATION FOR SEQ ID NO:   8:

(i) SEQUENCE CHARACTERISTICS:
        (A) LENGTH: 2065
        (B) TYPE: nucleic acid
        (C) STRANDEDNESS: single
        (D) TOPOLOGY: linear (xi) SEQUENCE DESCRIPTION:    SEQ ID NO: 8:

TAAGCTTGAT ATCGAATTCC CGCCCCCGGC TCGGGCTGTG AGGCGCTCGG GGCCGGGGTG        60

CGCGGCGGCG GCGGGCGGCG GAGGCTCCTG CTCGGCGGCG GCC                         103

ATG CGC GCG GGC CGG GGC GGC GTC CCG GGG AGC GGC GGC CTG AGG GCC         151
Met Arg Ala Gly Arg Gly Gly Val Pro Gly Ser Gly Gly Leu Arg Ala
5              10                  15

CGC CGC CGG CGC TGC TGC TGC TGC TGC TGG CGG ATG CTG CCG CCC GCC         199
Arg Arg Arg Arg Cys Cys Cys Cys Cys Trp Arg Met Leu Pro Pro Ala
20                  25                  30

GCC CCG GTC CCC GGC CCT GGC CGC GCT CCT GCG GGA CCC AGC GTG AGC         247
Ala Pro Val Pro Gly Pro Gly Arg Ala Pro Ala Gly Pro Ser Val Ser
35                  40                  45

CTC TAC CTG AGC GAG GAC GAG GTG CGC CGG CTG CTT GGT CTT GAT GCA         295
Leu Tyr Leu Ser Glu Asp Glu Val Arg Arg Leu Leu Gly Leu Asp Ala
50                  55                  60

GAG CTT TAC TAT GTG AGA AAT GAC CTC ATC AGT CAC TAC GCT CTG TCC         343
Glu Leu Tyr Tyr Val Arg Asn Asp Leu Ile Ser His Tyr Ala Leu Ser
65                  70                  75                  80

TTT AAC CTG CTA GTG CCC AGT GAG ACA AAC TTC CTG CAC TTC ACT TGG         391
Phe Asn Leu Leu Val Pro Ser Glu Thr Asn Phe Leu His Phe Thr Trp
85                  90                  95

CAT GCA AAG TCC AAG GTT GAA TAT AAG CTG GGA TTC CAA GTG AAC AAC         439
His Ala Lys Ser Lys Val Glu Tyr Lys Leu Gly Phe Gln Val Asn Asn
100                 105                 110

TTT GTG GCT ATG GGC ATG CCC CAG GTC AAT ATT TCT GCT CAA GGG GAG         487
Phe Val Ala Met Gly Met Pro Gln Val Asn Ile Ser Ala Gln Gly Glu
115                 120                 125
```

```
GGT CCA CGC ACT TTA TCA GTG TTT CGG GTC GAG CTT TCT TGT ACC GGC      535
Gly Pro Arg Thr Leu Ser Val Phe Arg Val Glu Leu Ser Cys Thr Gly
130             135             140

AAA GTC GAC TCT GAA GTC ATG ATT CTA ATG CAG CTC AAT CTG ACA GTG      583
Lys Val Asp Ser Glu Val Met Ile Leu Met Gln Leu Asn Leu Thr Val
145             150             155                         200

AAT TCC TCA AAA AAT TTT ACA GTT TTA AAT TTT AAA CGA AGG AAA ATG      631
Asn Ser Ser Lys Asn Phe Thr Val Leu Asn Phe Lys Arg Arg Lys Met
205             210             215

TGC TAC AAA AAA CTT GAA GAA GTA AAA ACT TCA GCC TTG GAC AAA AAC      679
Cys Tyr Lys Lys Leu Glu Glu Val Lys Thr Ser Ala Leu Asp Lys Asn
220             225             230

ACT AGC AGA ACT ATT TAT GAC CCT GTC CAT GCA GCG CCA ACG ACT TCC      727
Thr Ser Arg Thr Ile Tyr Asp Pro Val His Ala Ala Pro Thr Thr Ser
235             240             245

ACG CGT GTG TTT TAC ATC AGT GTA GGG GTT TGC TGT GCA GTG ATA TTT      775
Thr Arg Val Phe Tyr Ile Ser Val Gly Val Cys Cys Ala Val Ile Phe
250             255             260

CTT GTA GCA ATA ATA TTA GCC GTT TTG CAC CTT CAT AGC ATG AAA AGG      823
Leu Val Ala Ile Ile Leu Ala Val Leu His Leu His Ser Met Lys Arg
265             270             275             280

ATT GAA CTG GAT GAC AGC ATC AGC GCC AGC AGT AGT TCC CAG GGG CTG      871
Ile Glu Leu Asp Asp Ser Ile Ser Ala Ser Ser Ser Ser Gln Gly Leu
285             290             295

TCT CAG CCG TCT ACC CAG ACG ACC CAG TAT CTG AGA GCT GAC ACA CCC      919
Ser Gln Pro Ser Thr Gln Thr Thr Gln Tyr Leu Arg Ala Asp Thr Pro
300             305             310

AAC AAT GCA ACG CCT ATC ACC AGC TCC TCA GGT TAT CCT ACC TTG CGG      967
Asn Asn Ala Thr Pro Ile Thr Ser Ser Ser Gly Tyr Pro Thr Leu Arg
315             320             325

ATA GAG AAG AAC GAC TTG CGA AGT GTC ACT CTT CTG GAA GCC AAA GCC     1015
Ile Glu Lys Asn Asp Leu Arg Ser Val Thr Leu Leu Glu Ala Lys Ala
330             335             340

AAG GTG AAG GAT ATC GGA ATA TCC AGA GAA AGG ATC ACA CTG AAA GAT     1063
Lys Val Lys Asp Ile Gly Ile Ser Arg Glu Arg Ile Thr Leu Lys Asp
345             350             355             360

GTC CTC CAA GAA GGT AGT TTT GGG CGT ATT TTC CAT GGG ATT TTA GTA     1111
Val Leu Gln Glu Gly Ser Phe Gly Arg Ile Phe His Gly Ile Leu Val
365             370             375

GAT GAA AAA AGA CCA AAT AAA GAG AAG CAA ACA TTT GTA AAA ACA GTT     1159
Asp Glu Lys Arg Pro Asn Lys Glu Lys Gln Thr Phe Val Lys Thr Val
380             385             390

AAA GAC CAA GCA TCT GAA GTT CAG GTG ACG ATG ATG CTC ACC GAG AGC     1207
Lys Asp Gln Ala Ser Glu Val Gln Val Thr Met Met Leu Thr Glu Ser
395             400             405

TGC AAG CTT CGA GGT CTG CAC CAC AGA AAC CTC CTT CCT ATT ACT CAT     1255
Cys Lys Leu Arg Gly Leu His His Arg Asn Leu Leu Pro Ile Thr His
410             415             420

GTG TGC ATA GAA GAA GGA GAA AAG CCC ATG GTG GTA TTG CCA TAC ATG     1303
Val Cys Ile Glu Glu Gly Glu Lys Pro Met Val Val Leu Pro Tyr Met
425             430             435             440

AAT TGG GGG AAT CTT AAA TTA TTT CTT CGG CAG TGC AAA TTA GTA GAA     1351
Asn Trp Gly Asn Leu Lys Leu Phe Leu Arg Gln Cys Lys Leu Val Glu
445             450             455

GCC AAT AAT CCA CAG GCA ATT TCC CAG CAA GAT CTG GTC CAT ATG GCT     1399
Ala Asn Asn Pro Gln Ala Ile Ser Gln Gln Asp Leu Val His Met Ala
460             465             470

ATT CAG ATT GCC TGC GGG ATG AGC TAC CTG GCG AGG AGA GAA GTG ATC     1447
Ile Gln Ile Ala Cys Gly Met Ser Tyr Leu Ala Arg Arg Glu Val Ile
475             480             485
```

```
CAT AGA GAC CTG GCT GCT AGG AAC TGT GTC ATC GAC GAC ACT CTT CAA        1495
His Arg Asp Leu Ala Ala Arg Asn Cys Val Ile Asp Asp Thr Leu Gln
490                 495                 500

GTC AAG ATC ACA GAC AAT GCC CTT TCC AGA GAC TTG TTT CCT ATG GAC        1543
Val Lys Ile Thr Asp Asn Ala Leu Ser Arg Asp Leu Phe Pro Met Asp
505                 510                 515                 520

TAC CAC TGC CTA GGG GAC AAC GAG AAC AGG CCA GTG AGA TGG ATG GCT        1591
Tyr His Cys Leu Gly Asp Asn Glu Asn Arg Pro Val Arg Trp Met Ala
525                 530                 535                 540

CTG GAA AGT CTG GTT AAT AAT GAG TTC TCT AGT GCT AGT GAC GTG TGG        1639
Leu Glu Ser Leu Val Asn Asn Glu Phe Ser Ser Ala Ser Asp Val Trp
545                 550                 555

GCC TTT GGA GTG ACG CTG TGG GAG CTC ATG ACT CTG GGC CAG ACG CCC        1687
Ala Phe Gly Val Thr Leu Trp Glu Leu Met Thr Leu Gly Gln Thr Pro
560                 565                 570

TAC GTG GAC ATC GAC CCC TTT GAG ATG GCC GCT TAC CTG AAA GAT GGT        1735
Tyr Val Asp Ile Asp Pro Phe Glu Met Ala Ala Tyr Leu Lys Asp Gly
575                 580                 585

TAC CGA ATA GCC CAG CCA ATC AAC TGC CCT GAT GAA CTG TTT GCT GTG        1783
Tyr Arg Ile Ala Gln Pro Ile Asn Cys Pro Asp Glu Leu Phe Ala Val
590                 595                 600                 605

ATG GCC TGT TGC TGG GCC TTG GAC CCT GAG GAG AGG CCT AAG TTC CAG        1831
Met Ala Cys Cys Trp Ala Leu Asp Pro Glu Glu Arg Pro Lys Phe Gln
610                 615                 620

CAG CTG GTC CAG TGC CTC ACA GAG TTC CAC GCT GCC CTG GGA GCC TAC        1879
Gln Leu Val Gln Cys Leu Thr Glu Phe His Ala Ala Leu Gly Ala Tyr
625                 630                 635

GTC TGACTTCTCT CCCCATGCCG CCACTCAGAA GAAAGTGCCT GTCTGTCACG             1932
Val

GATGCCCCTC GTGCAGCGCA GTGCCTGCAG GGGCACACTG TCTCCAGATC ACCCAGCCTT      1992

AGCAGTGCTT CCAAACCTCA GCTTTTAACG ATGAAGTAAT AACGCAGAGT GTTTTCTAGA      2052

GTCGACCTGC AGG                                                        2065

(2) INFORMATION FOR SEQ ID NO:   9:

(i) SEQUENCE CHARACTERISTICS:
        (A) LENGTH: 566
        (B) TYPE: amino acid
        (D) TOPOLOGY: linear (vi) ORIGINAL SOURCE: mouse (xi) SEQUENCE DESCRIPTION:    SEQ ID NO: 9:

Met Leu Pro Pro Ala Ala Pro Val Pro Gly Pro Gly Arg Ala Pro Ala
                5                   10                  15

Gly Pro Ser Val Ser Leu Tyr Leu Ser Glu Asp Glu Val Arg Arg Leu
            20                  25                  30

Leu Gly Leu Asp Ala Glu Leu Tyr Val Arg Asn Asp Leu Ile Ser
        35                  40                  45

His Tyr Ala Leu Ser Phe Asn Leu Leu Val Pro Ser Glu Thr Asn Phe
    50                  55                  60

Leu His Phe Thr Trp His Ala Lys Ser Lys Val Glu Tyr Lys Leu Gly
65                  70                  75                  80

Phe Gln Val Asn Asn Phe Val Ala Met Gly Met Pro Gln Val Asn Ile
                85                  90                  95

Ser Ala Gln Gly Glu Gly Pro Arg Thr Leu Ser Val Phe Arg Val Glu
            100                 105                 110
```

-continued

```
Leu Ser Cys Thr Gly Lys Val Asp Ser Glu Val Met Ile Leu Met Gln
        115                 120                 125

Leu Asn Leu Thr Val Asn Ser Ser Lys Asn Phe Thr Val Leu Asn Phe
    130                 135                 140

Lys Arg Arg Lys Met Cys Tyr Lys Lys Leu Glu Glu Val Lys Thr Ser
145                 150                 155                 160

Ala Leu Asp Lys Asn Thr Ser Arg Thr Ile Tyr Asp Pro Val His Ala
                165                 170                 175

Ala Pro Thr Thr Ser Thr Arg Val Phe Tyr Ile Ser Val Gly Val Cys
            180                 185                 190

Cys Ala Val Ile Phe Leu Val Ala Ile Ile Leu Ala Val Leu His Leu
            195                 200                 205

His Ser Met Lys Arg Ile Glu Leu Asp Asp Ser Ile Ser Ala Ser Ser
    210                 215                 220

Ser Ser Gln Gly Leu Ser Gln Pro Ser Thr Gln Thr Thr Gln Tyr Leu
225                 230                 235                 240

Arg Ala Asp Thr Pro Asn Asn Ala Thr Pro Ile Thr Ser Ser Ser Gly
                245                 250                 255

Tyr Pro Thr Leu Arg Ile Glu Lys Asn Asp Leu Arg Ser Val Thr Leu
            260                 265                 270

Leu Glu Ala Lys Ala Lys Val Lys Asp Ile Gly Ile Ser Arg Glu Arg
            275                 280                 285

Ile Thr Leu Lys Asp Val Leu Gln Glu Gly Ser Phe Gly Arg Ile Phe
    290                 295                 300

His Gly Ile Leu Val Asp Glu Lys Arg Pro Asn Lys Glu Lys Gln Thr
305                 310                 315                 320

Phe Val Lys Thr Val Lys Asp Gln Ala Ser Glu Val Gln Val Thr Met
                325                 330                 335

Met Leu Thr Glu Ser Cys Lys Leu Arg Gly Leu His His Arg Asn Leu
            340                 345                 350

Leu Pro Ile Thr His Val Cys Ile Glu Glu Gly Glu Lys Pro Met Val
            355                 360                 365

Val Leu Pro Tyr Met Asn Trp Gly Asn Leu Leu Lys Leu Phe Leu Arg
    370                 375                 380

Gln Cys Lys Leu Val Glu Ala Asn Asn Pro Gln Ala Ile Ser Gln Gln
385                 390                 395                 400

Asp Leu Val His Met Ala Ile Gln Ile Ala Cys Gly Met Ser Tyr Leu
                405                 410                 415

Ala Arg Arg Val Ile His Arg Asp Leu Ala Ala Arg Asn Cys Val Ile
            420                 425                 430

Asp Asp Thr Leu Gln Val Lys Ile Thr Asp Asn Ala Leu Ser Arg Asp
    435                 440                 445

Leu Phe Pro Met Asp Tyr His Cys Leu Gly Asp Asn Glu Asn Arg Pro
    450                 455                 460

Val Arg Trp Met Ala Leu Glu Ser Leu Val Asn Asn Glu Phe Ser Ser
465                 470                 475                 480

Ala Ser Asp Val Trp Ala Phe Gly Val Thr Leu Trp Glu Leu Met Thr
                485                 490                 495

Leu Gly Gln Thr Pro Tyr Val Asp Ile Asp Pro Phe Glu Met Ala Ala
            500                 505                 510

Tyr Leu Lys Asp Gly Tyr Arg Ile Ala Gln Pro Ile Asn Cys Pro Asp
            515                 520                 525

Glu Leu Phe Ala Val Met Ala Cys Cys Trp Ala Leu Asp Pro Glu Glu
```

```
                530             535             540
Arg Pro Lys Phe Gln Gln Leu Val Gln Cys Leu Thr Glu Phe His Ala
545                 550                 555                 560

Ala Leu Gly Ala Tyr Val
            565
```

(2) INFORMATION FOR SEQ ID NO: 10:

(i) SEQUENCE CHARACTERISTICS:
        (A) LENGTH: 6
        (B) TYPE: amino acid
        (D) TOPOLOGY: linear (ii) MOLECULE TYPE: protein (xi) SEQUENCE DESCRIPTION:   SEQ ID NO: 10:

```
Asp Leu Ala Ala Arg Asn
            5
```

(2) INFORMATION FOR SEQ ID NO: 11:

(i) SEQUENCE CHARACTERISTICS:
        (A) LENGTH: 5
        (B) TYPE: amino acid
        (D) TOPOLOGY: linear (xi) SEQUENCE DESCRIPTION:   SEQ ID NO: 11:

```
Trp Met Ala Leu Glu
            5
```

(2) INFORMATION FOR SEQ ID NO: 12:

(i) SEQUENCE CHARACTERISTICS:
        (A) LENGTH: 9
        (B) TYPE: nucleic acid
        (C) STRANDEDNESS: single
        (D) TOPOLOGY: linear (xi) SEQUENCE DESCRIPTION:   SEQ ID NO: 12:

```
CCRCCATGG                                                                9
```

(2) INFORMATION FOR SEQ ID NO: 13:

(i) SEQUENCE CHARACTERISTICS:
        (A) LENGTH: 6
        (B) TYPE: amino acid
        (D) TOPOLOGY: linear (ii) MOLECULE TYPE: protein (xi) SEQUENCE DESCRIPTION:   SEQ ID NO: 13:

```
Gln Glu Gly Thr Phe Gly
            5
```

(2) INFORMATION FOR SEQ ID NO: 14:

(i) SEQUENCE CHARACTERISTICS:
        (A) LENGTH: 8
        (B) TYPE: amino acid
        (D) TOPOLOGY: linear (ii) MOLECULE TYPE: protein (xi) SEQUENCE DESCRIPTION:   SEQ ID NO: 14:

```
His Arg Asp Leu Ala Ala Arg Asn
            5
```

(2) INFORMATION FOR SEQ ID NO: 15:

(i) SEQUENCE CHARACTERISTICS:
        (A) LENGTH: 7
        (B) TYPE: amino acid
        (D) TOPOLOGY: linear (ii) MOLECULE TYPE: protein (xi) SEQUENCE DESCRIPTION:    SEQ ID NO: 15:

Arg Trp Met Ala Leu Glu Ser
                5

(2) INFORMATION FOR SEQ ID NO: 16:

(i) SEQUENCE CHARACTERISTICS:
        (A) LENGTH: 8
        (B) TYPE: amino acid
        (D) TOPOLOGY: linear (ii) MOLECULE TYPE: protein (xi) SEQUENCE DESCRIPTION:    SEQ ID NO: 16:

His Ala Ala Leu Gly Ala Tyr Val
                5

(2) INFORMATION FOR SEQ ID NO: 17:

(i) SEQUENCE CHARACTERISTICS:
        (A) LENGTH: 8
        (B) TYPE: amino acid
        (D) TOPOLOGY: linear (ii) MOLECULE TYPE: protein (xi) SEQUENCE DESCRIPTION:    SEQ ID NO: 17:

Val Asn Ser Leu Trp Glu Leu Met
                5

(2) INFORMATION FOR SEQ ID NO: 18:

(i) SEQUENCE CHARACTERISTICS:
        (A) LENGTH: 7
        (B) TYPE: amino acid
        (D) TOPOLOGY: linear (ii) MOLECULE TYPE: protein (xi) SEQUENCE DESCRIPTION:    SEQ ID NO: 18:

Val Thr Leu Trp Glu Leu Met
                5

(2) INFORMATION FOR SEQ ID NO: 19:

(i) SEQUENCE CHARACTERISTICS:
        (A) LENGTH: 20
        (B) TYPE: amino acid
        (D) TOPOLOGY: linear (ii) MOLECULE TYPE: protein (xi) SEQUENCE DESCRIPTION:    SEQ ID NO: 19:

Lys Phe Gln Gln Leu Val Gln Cys Leu Thr Glu Phe His Ala Ala Leu
               5                   10                 15
Gly Ala Tyr Val
        20

(2) INFORMATION FOR SEQ ID NO: 20:

(i) SEQUENCE CHARACTERISTICS:
        (A) LENGTH: 606
        (B) TYPE: amino acid
        (D) TOPOLOGY: linear (ii) MOLECULE TYPE:    protein (vi) ORIGINAL SOURCE:  human (xi) SEQUENCE DESCRIPTION:    SEQ ID NO: 20:

Met Arg Gly Ala Ala Arg Leu Gly Arg Pro Gly Arg Ser Cys Leu Pro
                 5                  10                  15

Gly Pro Ala Leu Arg Ala Ala Ala Pro Ala Leu Leu Leu Ala Arg
             20                  25                  30

Cys Ala Val Ala Ala Ala Ala Gly Leu Arg Ala Ala Ala Arg Pro Arg
             35                  40                  45

Pro Pro Glu Leu Gln Ser Ala Ser Ala Gly Pro Ser Val Ser Leu Tyr
             50                  55                  60

Leu Ser Glu Asp Glu Val Arg Arg Leu Ile Gly Leu Asp Ala Glu Leu
65                   70                  75                  80

Tyr Tyr Val Arg Asn Asp Leu Ile Ser His Tyr Ala Leu Ser Phe Asn
                 85                  90                  95

Leu Leu Val Pro Ser Glu Thr Asn Phe Leu His Phe Thr Trp His Ala
             100                 105                 110

Lys Ser Lys Val Glu Tyr Lys Leu Gly Phe Gln Val Asp Asn Val Leu
             115                 120                 125

Ala Met Asp Met Pro Gln Val Asn Ile Ser Val Gln Gly Glu Val Pro
             130                 135                 140

Arg Thr Leu Ser Val Phe Arg Val Glu Leu Ser Cys Thr Gly Lys Val
145                 150                 155                 160

Asp Ser Glu Val Met Ile Leu Met Gln Leu Asn Leu Thr Val Asn Ser
                 165                 170                 175

Ser Lys Asn Phe Thr Val Leu Asn Phe Lys Arg Arg Lys Met Cys Tyr
             180                 185                 190

Lys Lys Leu Glu Glu Val Lys Thr Ser Ala Leu Asp Lys Asn Thr Ser
             195                 200                 205

Arg Thr Ile Tyr Asp Pro Val His Ala Ala Pro Thr Thr Ser Thr Arg
             210                 215                 220

Val Phe Tyr Ile Ser Val Gly Val Cys Cys Ala Val Ile Phe Leu Val
225                 230                 235                 240

Ala Ile Ile Leu Ala Val Leu His Leu His Asn Met Lys Arg Ile Glu
                 245                 250                 255

Leu Asp Asp Ser Ile Ser Ala Ser Ser Ser Gln Gly Leu Ser Gln
             260                 265                 270

Pro Ser Thr Gln Thr Thr Gln Tyr Leu Arg Ala Asp Thr Pro Asn Asn
             275                 280                 285

Ala Thr Pro Ile Thr Ser Tyr Pro Thr Leu Arg Ile Glu Lys Asn Asp
             290                 295                 300

Leu Arg Ser Val Thr Leu Leu Glu Ala Lys Gly Lys Val Lys Asp Ile
305                 310                 315                 320

Ala Ile Ser Arg Glu Arg Ile Thr Leu Lys Asp Val Leu Gln Glu Gly
                 325                 330                 335

Thr Phe Gly Arg Ile Phe His Gly Ile Leu Ile Asp Glu Lys Asp Pro
             340                 345                 350

Asn Lys Glu Lys Gln Ala Phe Val Lys Thr Val Lys Asp Gln Ala Ser

-continued

```
            355                 360                 365
Glu Ile Gln Val Thr Met Met Leu Thr Glu Ser Cys Lys Leu Arg Gly
370                 375                 380

Leu His His Arg Asn Leu Leu Pro Ile Thr His Val Cys Ile Glu Glu
385                 390                 495                 400

Gly Glu Lys Pro Met Val Ile Leu Pro Tyr Met Asn Trp Gly Asn Leu
                    405                 410                 415

Lys Leu Phe Leu Arg Gln Cys Lys Leu Val Glu Ala Asn Asn Pro Gln
            420                 425                 430

Ala Ile Ser Gln Gln Asp Leu Val His Met Ala Ile Gln Ile Ala Cys
                435                 440                 445

Gly Met Ser Tyr Leu Ala Arg Arg Glu Val Ile His Lys Asp Leu Ala
450                 455                 460

Ala Arg Asn Cys Val Ile Asp Asp Thr Leu Gln Val Lys Ile Thr Asp
465                 470                 475                 480

Asn Ala Leu Ser Arg Asp Leu Phe Pro Met Asp Tyr His Cys Leu Gly
                485                 490                 495

Asp Asn Glu Asn Arg Pro Val Arg Trp Met Ala Leu Glu Ser Leu Val
            500                 505                 510

Asn Asn Glu Phe Ser Ser Ala Ser Asp Val Trp Ala Phe Gly Val Asn
            515                 520                 525

Ser Leu Trp Glu Leu Met Thr Leu Gly Gln Thr Pro Tyr Thr Leu Asp
530                 535                 540

Ile Asp Pro Phe Glu Met Ala Ala Tyr Leu Lys Asp Gly Tyr Arg Ile
545                 550                 555                 560

Ala Gln Pro Ile Thr Cys Pro Asp Glu Leu Phe Ala Val Met Ala Cys
                565                 570                 575

Cys Trp Ala Leu Asp Pro Glu Glu Arg Pro Arg Phe Gln Gln Leu Val
            580                 585                 590

Gln Cys Leu Thr Glu Phe His Ala Ala Leu Gly Ala Tyr Val
        595                 600                 605
```

(2) INFORMATION FOR SEQ ID NO: 21:

(i) SEQUENCE CHARACTERISTICS:
        (A) LENGTH:593
        (B) TYPE: amino acid
        (D) TOPOLOGY: linear (ii) MOLECULE TYPE:    protein (vi) ORIGINAL SOURCE:   human (xi) SEQUENCE DESCRIPTION:   SEQ ID NO: 21:

```
Met Arg Ala Gly Arg Gly Gly Val Pro Ser Gly Gly Leu Arg Ala Arg
                5                  10                  15

Arg Arg Arg Cys Cys Cys Cys Trp Arg Met Leu Pro Pro Ala
            20                  25                  30

Ala Pro Val Pro Gly Pro Gly Arg Ala Pro Ala Gly Pro Ser Val Ser
                35                  40                  45

Leu Tyr Leu Ser Glu Asp Glu Val Arg Arg Leu Leu Gly Leu Asp Ala
            50                  55                  60

Glu Leu Tyr Tyr Val Arg Asn Asp Leu Ile Ser His Tyr Ala Leu Ser
65                  70                  75                  80

Phe Asn Leu Leu Val Pro Ser Glu Thr Asn Phe Leu His Phe Thr Trp
                85                  90                  95
```

-continued

```
His Ala Lys Ser Lys Val Glu Tyr Lys Leu Gly Phe Gln Val Asn Asn
            100                 105                 110

Phe Val Ala Met Gly Met Pro Gln Val Asn Ile Ser Ala Gln Gly Glu
        115                 120                 125

Gly Pro Arg Thr Leu Ser Val Phe Arg Val Glu Leu Ser Cys Thr Gly
    130                 135                 140

Lys Val Asp Ser Glu Val Met Ile Leu Met Gln Leu Asn Leu Thr Val
145                 150                 155                 160

Asn Ser Ser Lys Asn Phe Thr Val Leu Asn Phe Lys Arg Arg Lys Met
                165                 170                 175

Cys Tyr Lys Lys Leu Glu Glu Val Lys Thr Ser Ala Leu Asp Lys Asn
            180                 185                 190

Thr Ser Arg Thr Ile Tyr Asp Pro Val His Ala Ala Pro Thr Thr Ser
        195                 200                 205

Thr Arg Val Phe Tyr Ile Ser Val Gly Val Cys Cys Ala Val Ile Phe
    210                 215                 220

Leu Val Ala Ile Ile Leu Ala Val Leu His Leu His Ser Met Lys Arg
225                 230                 235                 240

Ile Glu Leu Asp Asp Ser Ile Ser Ala Ser Ser Ser Gln Gly Leu
                245                 250                 255

Ser Gln Pro Ser Thr Gln Thr Thr Gln Tyr Leu Arg Ala Asp Thr Pro
            260                 265                 270

Asn Asn Ala Thr Pro Ile Thr Ser Ser Ser Gly Tyr Pro Thr Leu Arg
        275                 280                 285

Ile Glu Lys Asn Asp Leu Arg Ser Val Thr Leu Leu Glu Ala Lys Ala
    290                 295                 300

Lys Val Lys Asp Ile Gly Ile Ser Arg Glu Arg Ile Thr Leu Lys Asp
305                 310                 315                 320

Val Leu Gln Glu Gly Ser Phe Gly Arg Ile Phe His Gly Ile Leu Val
                325                 330                 335

Asp Glu Lys Arg Pro Asn Lys Glu Lys Gln Thr Phe Val Lys Thr Val
            340                 345                 350

Lys Asp Gln Ala Ser Glu Val Gln Val Thr Met Met Leu Thr Glu Ser
        355                 360                 365

Cys Lys Leu Arg Gly Leu His His Arg Asn Leu Leu Pro Ile Thr His
    370                 375                 380

Val Cys Ile Glu Glu Gly Glu Lys Pro Met Val Val Leu Pro Tyr Met
385                 390                 395                 400

Asn Trp Gly Asn Leu Lys Leu Phe Leu Arg Gln Cys Lys Leu Val Glu
                405                 410                 415

Ala Asn Asn Pro Gln Ala Ile Ser Gln Gln Asp Leu Val His Met Ala
            420                 425                 430

Ile Gln Ile Ala Cys Gly Met Ser Tyr Leu Ala Arg Arg Glu Val Ile
        435                 440                 445

His Arg Asp Leu Ala Ala ARg Asn Cys Val Ile Asp Asp Thr Leu Gln
    450                 455                 460

Val Lys Ile Thr Asp Asn Ala Leu Ser Arg Asp Leu Phe Pro Met Asp
465                 470                 475                 480

Tyr His Cys Leu Gly Asp Asn Glu Asn Arg Pro Val Arg Trp Met Ala
                485                 490                 495

Leu Glu Ser Leu Val Asn Asn Glu Phe Ser Ser Ala Ser Asp Val Trp
            500                 505                 510

Ala Phe Gly Val Thr Leu Trp Glu Leu Met Thr Leu Gly Gln Thr Pro
```

```
                  515                 520                 525
Tyr Val Asp Ile Asp Pro Phe Glu Met Ala Ala Tyr Leu Lys Asp Gly
        530                 535                 540

Tyr Arg Ile Ala Gln Pro Ile Asn Cys Pro Asp Glu Leu Phe Ala Val
545                 550                 555                 560

Met Ala Cys Cys Trp Ala Leu Asp Pro Glu Glu Arg Pro Lys Phe Gln
                565                 570                 575

Gln Leu Val Gln Cys Leu Thr Glu Phe His Ala Ala Leu Gly Ala Tyr
                580                 585                 590

Val
```